(12) United States Patent
Chen

(10) Patent No.: US 10,874,454 B2
(45) Date of Patent: *Dec. 29, 2020

(54) MULTI-POLE SYNCHRONOUS PULMONARY ARTERY RADIOFREQUENCY ABLATION CATHETER

(71) Applicant: PULNOVO MEDICAL (WUXI) CO., LTD., Jiangsu (CN)

(72) Inventor: Shaoliang Chen, Nanjing (CN)

(73) Assignee: PULNOVO MEDICAL (WUXI) CO., LTD., Wuxi (CN)

(*) Notice: Subject to any disclaimer, the term of this patent is extended or adjusted under 35 U.S.C. 154(b) by 893 days.

This patent is subject to a terminal disclaimer.

(21) Appl. No.: 15/228,358

(22) Filed: Aug. 4, 2016

(65) Prior Publication Data
US 2016/0338774 A1    Nov. 24, 2016

Related U.S. Application Data

(63) Continuation of application No. 14/530,588, filed on Oct. 31, 2014, now abandoned, which is a (Continued)

(30) Foreign Application Priority Data

Nov. 13, 2012  (CN) .......................... 2012 1 0453470
Mar. 27, 2013  (CN) .......................... 2013 1 0103141

(51) Int. Cl.
*A61B 18/12* (2006.01)
*A61B 18/14* (2006.01)
(Continued)

(52) U.S. Cl.
CPC .......... *A61B 18/1492* (2013.01); *A61B 18/00* (2013.01); *A61M 25/0147* (2013.01);
(Continued)

(58) Field of Classification Search
CPC ............ A61B 2018/00386; A61B 2018/00577
See application file for complete search history.

(56) References Cited

U.S. PATENT DOCUMENTS 5,263,493 A  11/1993 Avitall
5,643,197 A   7/1997 Brucker et al.
(Continued)

FOREIGN PATENT DOCUMENTS

AU    2007290727 B2   1/2012
CN      102119009 A   7/2011
(Continued)

OTHER PUBLICATIONS

Pokushalov, Evgeny, et al. "A Randomized Comparison of Pulmonary Vein Isolation . . . " Journal of the American College of Cardiology, vol. 60, No. 13, Sep. 25, 2012,pp. 1163-1170 (Year: 2012).*

(Continued)

*Primary Examiner* — Jaymi E Della
(74) *Attorney, Agent, or Firm* — Wilson Sonsini Goodrich and Rosati, P.C.

(57) ABSTRACT

Systems, devices, and method for performing pulmonary artery denervation are disclosed. An ablation device is positioned in a pulmonary artery trunk of a patient. Target tissue is ablated in the pulmonary artery trunk under conditions effective to affect a reduction in mean pulmonary artery pressure and systolic pulmonary artery pressure. The target tissue includes at least one of the distal portion of the main pulmonary artery, the proximal portion of the left pulmonary artery, or the proximal portion of the right pulmonary artery.

27 Claims, 16 Drawing Sheets

Related U.S. Application Data continuation of application No. 14/079,230, filed on Nov. 13, 2013, now abandoned.

(51) Int. Cl.

| | | |
|---|---|---|
| *A61N 1/06* | (2006.01) | |
| *A61B 18/00* | (2006.01) | |
| *A61M 25/01* | (2006.01) | |
| *A61N 7/02* | (2006.01) | |
| *A61B 17/00* | (2006.01) | |
| *A61N 7/00* | (2006.01) | |

(52) U.S. Cl.
CPC ............... *A61N 1/06* (2013.01); *A61N 7/02* (2013.01); *A61B 2017/00323* (2013.01); *A61B 2017/00867* (2013.01); *A61B 2018/00029* (2013.01); *A61B 2018/00166* (2013.01); *A61B 2018/00214* (2013.01); *A61B 2018/00375* (2013.01); *A61B 2018/00404* (2013.01); *A61B 2018/00577* (2013.01); *A61B 2018/00791* (2013.01); *A61B 2018/00797* (2013.01); *A61B 2018/00821* (2013.01); *A61B 2018/1407* (2013.01); *A61B 2018/1467* (2013.01); *A61B 2218/002* (2013.01); *A61N 2007/003* (2013.01); *F04C 2270/041* (2013.01)

(56) References Cited

U.S. PATENT DOCUMENTS

| | | |
|---|---|---|
| 5,715,817 A | 2/1998 | Stevens-Wright et al. |
| 5,782,900 A | 7/1998 | De La Rama et al. |
| 5,830,214 A | 11/1998 | Flom et al. |
| 5,833,604 A | 11/1998 | Houser et al. |
| 5,836,947 A | 11/1998 | Fleischman et al. |
| 5,913,856 A | 6/1999 | Chia et al. |
| 5,919,188 A | 7/1999 | Shearon et al. |
| 5,938,694 A | 8/1999 | Jaraczewski et al. |
| 6,064,902 A | 5/2000 | Haissaguerre et al. |
| 6,090,104 A | 7/2000 | Webster, Jr. |
| 6,096,036 A | 8/2000 | Bowe et al. |
| 6,115,626 A | 9/2000 | Whayne et al. |
| 6,123,702 A | 9/2000 | Swanson et al. |
| 6,198,974 B1 | 3/2001 | Webster, Jr. |
| 6,237,886 B1 | 5/2001 | Katsumata et al. |
| 6,292,695 B1 | 9/2001 | Webster, Jr. et al. |
| 6,411,852 B1 | 6/2002 | Danek et al. |
| 6,493,589 B1 | 12/2002 | Medhkour et al. |
| 6,564,096 B2 | 5/2003 | Mest |
| 6,575,969 B1* | 6/2003 | Rittman, III ....... A61B 18/1482 128/898 |
| 6,690,971 B2 | 2/2004 | Schauerte et al. |
| 7,260,431 B2 | 8/2007 | Libbus et al. |
| 7,269,457 B2 | 9/2007 | Shafer et al. |
| 7,363,076 B2 | 4/2008 | Yun et al. |
| 7,367,951 B2 | 5/2008 | Bennett et al. |
| 7,587,238 B2 | 9/2009 | Moffitt et al. |
| 7,616,990 B2 | 11/2009 | Chavan et al. |
| 7,623,926 B2 | 11/2009 | Rossing et al. |
| 7,630,760 B2 | 12/2009 | Libbus et al. |
| 7,664,548 B2 | 2/2010 | Amurthur et al. |
| 7,711,430 B2 | 5/2010 | Errico et al. |
| 7,715,915 B1 | 5/2010 | Ryu et al. |
| 7,734,355 B2 | 6/2010 | Cohen et al. |
| 7,744,618 B2 | 6/2010 | Shuros et al. |
| 7,783,353 B2 | 8/2010 | Libbus et al. |
| 7,789,877 B2 | 9/2010 | Vanney |
| 7,801,604 B2 | 9/2010 | Brockway et al. |
| 7,826,899 B1 | 11/2010 | Ryu et al. |
| 7,828,795 B2 | 11/2010 | Privitera et al. |
| 7,899,527 B2 | 3/2011 | Yun et al. |
| 7,925,342 B2 | 4/2011 | Amurthur et al. |
| 7,937,147 B2 | 5/2011 | Sih et al. |
| 8,019,435 B2 | 9/2011 | Hastings et al. |
| 8,027,724 B2 | 9/2011 | Wei et al. |
| 8,052,668 B2 | 11/2011 | Sih |
| 8,073,538 B2 | 12/2011 | Peters et al. |
| 8,088,127 B2 | 1/2012 | Mayse et al. |
| 8,249,705 B1 | 8/2012 | Kieval et al. |
| 9,005,100 B2 | 4/2015 | Gnanashanmugam et al. |
| 9,028,391 B2 | 5/2015 | Gnanashanmugam et al. |
| 2001/0031987 A1 | 10/2001 | Saksena et al. |
| 2002/0065514 A1 | 5/2002 | Rashidi |
| 2002/0120304 A1 | 8/2002 | Mest |
| 2004/0133197 A1* | 7/2004 | Utley ................ A61B 18/1477 606/41 |
| 2005/0004440 A1 | 1/2005 | Vanney |
| 2005/0004565 A1 | 1/2005 | Vanney |
| 2005/0010095 A1 | 1/2005 | Stewart et al. |
| 2005/0113822 A1 | 5/2005 | Fuimaono et al. |
| 2005/0261672 A1 | 11/2005 | Deem et al. |
| 2005/0283148 A1 | 12/2005 | Janssen et al. |
| 2006/0041277 A1 | 2/2006 | Deem et al. |
| 2006/0074272 A1 | 4/2006 | Diubaldi |
| 2006/0116737 A1 | 6/2006 | Libbus |
| 2006/0167498 A1 | 7/2006 | DiLorenzo |
| 2006/0217772 A1 | 9/2006 | Libbus et al. |
| 2006/0241366 A1 | 10/2006 | Falwell et al. |
| 2007/0032835 A1 | 2/2007 | Rittman, III |
| 2007/0038055 A1 | 2/2007 | Fuimaono et al. |
| 2007/0060921 A1 | 3/2007 | Janssen et al. |
| 2007/0083193 A1 | 4/2007 | Werneth et al. |
| 2007/0083194 A1 | 4/2007 | Kunis et al. |
| 2007/0129720 A1 | 6/2007 | Demarais et al. |
| 2007/0129760 A1 | 6/2007 | Demarais et al. |
| 2007/0142879 A1 | 6/2007 | Greenberg et al. |
| 2007/0191904 A1 | 8/2007 | Libbus et al. |
| 2007/0225641 A1 | 9/2007 | Schneider et al. |
| 2007/0255379 A1 | 11/2007 | Williams et al. |
| 2008/0255642 A1 | 10/2008 | Zarins et al. |
| 2008/0281312 A1 | 11/2008 | Werneth et al. |
| 2008/0306570 A1 | 12/2008 | Rezai et al. |
| 2009/0024124 A1 | 1/2009 | Lefler et al. |
| 2009/0062873 A1 | 3/2009 | Wu et al. |
| 2009/0118780 A1 | 5/2009 | DiLorenzo |
| 2009/0177262 A1 | 7/2009 | Oberti et al. |
| 2009/0216290 A1 | 8/2009 | Ruse et al. |
| 2009/0254142 A1 | 10/2009 | Edwards et al. |
| 2010/0057074 A1 | 3/2010 | Roman et al. |
| 2010/0094196 A1 | 4/2010 | Nash et al. |
| 2010/0113928 A1 | 5/2010 | Thapliyal et al. |
| 2010/0114095 A1 | 5/2010 | Janssen et al. |
| 2010/0137860 A1 | 6/2010 | Demarais et al. |
| 2010/0152726 A1 | 6/2010 | Cadouri et al. |
| 2010/0168548 A1 | 7/2010 | Govari et al. |
| 2010/0217347 A1 | 8/2010 | Swoyer et al. |
| 2010/0222859 A1 | 9/2010 | Govari et al. |
| 2010/0228317 A1 | 9/2010 | Libbus et al. |
| 2010/0241188 A1 | 9/2010 | Errico et al. |
| 2010/0249568 A1 | 9/2010 | Stehr et al. |
| 2010/0249773 A1 | 9/2010 | Clark et al. |
| 2010/0249859 A1 | 9/2010 | Dilorenzo |
| 2010/0268307 A1 | 10/2010 | Demarais et al. |
| 2010/0274221 A1 | 10/2010 | Sigg et al. |
| 2010/0286684 A1 | 11/2010 | Hata et al. |
| 2010/0286734 A1 | 11/2010 | Yun et al. |
| 2010/0298905 A1 | 11/2010 | Simon |
| 2011/0034915 A1 | 2/2011 | Ibrahim et al. |
| 2011/0118725 A1 | 5/2011 | Mayse et al. |
| 2011/0152855 A1 | 6/2011 | Mayse et al. |
| 2011/0160720 A1 | 6/2011 | Johnson |
| 2011/0178569 A1 | 7/2011 | Parnis et al. |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0257708 A1 | 10/2011 | Kramer et al. |
| 2011/0276103 A1 | 11/2011 | Maile et al. |
| 2011/0301587 A1 | 12/2011 | Deem et al. |
| 2011/0301679 A1 | 12/2011 | Rezai et al. |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |

(56) References Cited

U.S. PATENT DOCUMENTS

| | | |
|---|---|---|
| 2012/0029512 A1 | 2/2012 | Willard et al. |
| 2012/0065554 A1 | 3/2012 | Pikus |
| 2012/0116382 A1 | 5/2012 | Ku et al. |
| 2012/0123258 A1 | 5/2012 | Willard |
| 2012/0123406 A1 | 5/2012 | Edmunds et al. |
| 2012/0143294 A1 | 6/2012 | Clark et al. |
| 2012/0157992 A1 | 6/2012 | Smith et al. |
| 2012/0157993 A1 | 6/2012 | Jenson et al. |
| 2012/0158104 A1 | 6/2012 | Huynh et al. |
| 2012/0165815 A1 | 6/2012 | Collins et al. |
| 2012/0172680 A1 | 7/2012 | Gelfand et al. |
| 2012/0172870 A1 | 7/2012 | Jenson et al. |
| 2012/0184952 A1 | 7/2012 | Jenson et al. |
| 2012/0232551 A1 | 9/2012 | Swanson et al. |
| 2012/0272839 A1 | 11/2012 | Kaneko |
| 2012/0277839 A1 | 11/2012 | Kramer et al. |
| 2012/0290024 A1 | 11/2012 | Zhang et al. |
| 2012/0294424 A1 | 11/2012 | Chin et al. |
| 2012/0302909 A1 | 11/2012 | Mayse et al. |
| 2013/0131743 A1 | 5/2013 | Yamasaki et al. |
| 2013/0165922 A1 | 6/2013 | Falwell et al. |
| 2013/0204068 A1* | 8/2013 | Gnanashanmugam ............ A61N 5/1002 600/1 |
| 2013/0317375 A1 | 11/2013 | Garcia et al. |
| 2014/0180277 A1 | 6/2014 | Chen |
| 2015/0057599 A1 | 2/2015 | Chen |
| 2015/0196357 A1 | 7/2015 | Chen |
| 2015/0201988 A1 | 7/2015 | Chen |
| 2015/0272656 A1 | 10/2015 | Chen |
| 2015/0272668 A1 | 10/2015 | Chen |
| 2016/0128767 A1* | 5/2016 | Azamian ............ A61B 18/1492 606/41 |
| 2018/0140347 A1 | 5/2018 | Chen |

FOREIGN PATENT DOCUMENTS

| | | |
|---|---|---|
| CN | 102198015 A | 9/2011 |
| CN | 102641153 A | 8/2012 |
| CN | 102651153 A | 8/2012 |
| CN | 102686179 A | 9/2012 |
| CN | 102908191 A | 2/2013 |
| CN | 103142304 A | 6/2013 |
| CN | 202982207 U | 6/2013 |
| CN | 103908336 A | 7/2014 |
| EP | 0467422 B1 | 12/1997 |
| EP | 0916360 A2 | 5/1999 |
| EP | 1637086 A1 | 3/2006 |
| EP | 2712567 A1 | 4/2014 |
| JP | 2000500363 A | 1/2000 |
| JP | 2006504473 A | 2/2006 |
| JP | 2008245767 A | 10/2008 |
| JP | 2009543607 A | 12/2009 |
| JP | 2011224364 A | 11/2011 |
| JP | 2013510676 A | 3/2013 |
| RU | 2074645 C1 | 3/1997 |
| RU | 2102090 C1 | 1/1998 |
| RU | 2503408 C2 | 1/2014 |
| SU | 1119663 A1 | 10/1984 |
| SU | 1412745 A1 | 7/1988 |
| SU | 1734708 A1 | 5/1992 |
| WO | WO-9301862 A1 | 2/1993 |
| WO | WO-9505771 A1 | 3/1995 |
| WO | WO-9965561 A1 | 12/1999 |
| WO | WO-0137723 A2 | 5/2001 |
| WO | WO-0137925 A2 | 5/2001 |
| WO | WO-2010110785 A1 | 9/2010 |
| WO | WO-2011075328 A1 | 6/2011 |
| WO | WO-2011091069 A1 | 7/2011 |
| WO | WO-2011139589 A2 | 11/2011 |
| WO | WO-2012068268 A2 | 5/2012 |
| WO | WO-2012120495 A2 | 9/2012 |
| WO | WO-2012149341 A1 | 11/2012 |
| WO | WO-2012149511 A2 | 11/2012 |
| WO | WO-2012154800 A1 | 11/2012 |
| WO | WO-2014075415 A1 | 5/2014 |
| WO | WO-2016007851 A1 | 1/2016 |

OTHER PUBLICATIONS

EP15818364.0 Extended Search Report dated Mar. 9, 2018.

U.S. Appl. No. 14/672,021 Notice of Allowance dated Nov. 22, 2017.

Notice of Allowance dated Sep. 11, 2017 for U.S. Appl. No. 14/672,010.

Notice of Allowance dated Sep. 14, 2017 and Sep. 22, 2017 for U.S. Appl. No. 14/672,021.

Notice of Allowance dated Sep. 19, 2017 and Sep. 7, 2017 for U.S. Appl. No. 14/666,214.

Office Action dated Aug. 31, 2017 for U.S. Appl. No. 14/672,013.

European Search Report dated Nov. 16, 2016 for EP Application No. 13840133.6.

Office Action dated Oct. 21, 2016 for U.S. Appl. No. 14/530,588.

Notice of Allowance dated Sep. 22, 2017 for U.S. Appl. No. 14/672,021.

Notice of Allowance dated Oct. 13, 2017 for U.S. Appl. No. 14/672,010.

Notice of Allowance dated Oct. 13, 2017 for U.S. Appl. No. 14/666,214.

Notice of Allowance dated Oct. 13, 2017 for U.S. Appl. No. 14/672,021.

Notice of Allowance dated Oct. 18, 2017 for U.S. Appl. No. 14/672,013.

Notice of Allowance dated Nov. 2, 2017 for U.S. Appl. No. 14/672,013.

Chen, SL. et al., Hemodynamic, functional, and clinical responses to pulmonary artery denervation in patients with pulmonary arterial hypertension of different causes: phase II results from the Pulmonary Artery Denervation-1 study. Circ Cardiovasc Interv. Nov. 2015;8(11):e002837. doi: 10.1161/CIRCINTERVENTIONS.115.002837.

Chen, SL. et al., Response to Letter Regarding Article, "Hemodynamic, Functional, and Clinical Responses to Pulmonary Artery Denervation in Patients With Pulmonary Arterial Hypertension of Different Causes: Phase II Results From the Pulmonary Artery Denervation-1 Study". Circ Cardiovasc Interv. Jan. 2016;9(1):e003463. doi: 10.1161/CIRCINTERVENTIONS.115.003463. No abstract available.

Chen,SL. et al., Pericardial effusion is correlated with clinical outcome after pulmonary artery denervation for pulmonary arterial hypertension. Oncotarget. Dec. 20, 2016. doi: 10.18632/oncotarget.14031. [Epub ahead of print].

Zhang, H. et al., Pulmonary artery denervation for treatment of a patient with pulmonary hypertension secondary to left heart disease. Pulm Circ. Jun. 2016;6(2):240-3. doi: 10.1086/685550.

Zhang, YJ. et al., Pulmonary arterial hypertension: pharmacologic therapies and potential pulmonary artery denervation treatment. EuroIntervention. May 2013;9 Suppl R:R149-54. doi: 10.4244/EIJV9SRA25. Review.

Benza, et al. Predicting survival in pulmonary arterial hypertension: insights from the Registry to Evaluate Early and Long-Term Pulmonary Arterial Hypertension Disease Management (REVEAL). Circulation. Jul. 13, 2010;122(2):164-72. doi: 10.1161/Circulationaha.109.898122. Epub Jun. 28, 2010.

Brace. Radiofrequency and microwave ablation of the liver, lung, kidney, and bone: what are the differences? Curr Probl Diagn Radiol. May-Jun. 2009;38(3):135-43. doi: 10.1067/j.cpradiol.2007.10.001.

Chen, et al. Percutaneous pulmonary artery denervation completely abolishes experimental pulmonary arterial hypertension in vivo. EuroIntervention. Jun. 22, 2013;9(2):269-76. doi: 10.4244/EIJV9I2A43.

Chen, et al. Pulmonary artery denervation to treat pulmonary arterial hypertension: the single-center, prospective, first-in-man PADN-1 study (first-in-man pulmonary artery denervation for treat-

(56) References Cited

OTHER PUBLICATIONS ment of pulmonary artery hypertension). J Am Coll Cardiol. Sep. 17, 2013;62(12):1092-100. doi: 10.1016/j.jacc.2013.05.075. Epub Jul. 10, 2013.
Chen. Pulmonary artery denervaion to treat pulmonary arterial hypertension unresponive to medication: a single-center, prospective, first-in-man PADN1 study. Nanjing First Hospital, Nanjing Medical University, Nanjing, China. TCT2012. Oct. 22, 2012. 23 pages.
Chinese Clinical Trial Register (ChiCTR): "First-in-Man of Pulmonary artery denervation for treatment of pulmonary artery hypertention: the PADN-1 trial" dated Apr. 6, 2012, http://www.chictr.org/en/proj/show.aspx?proj=2741 (3 pages).
Chinese Clinical Trial Register (ChiCTR): "Percutaneous pulmonary arterial denervation for treatment of chronic heart failure with secondary pulmonary hypertension" dated Nov. 2, 2012, http://www.chictr.org/en/proj/show.aspx? proj=3677 (3 pages).
Chinese Clinical Trial Register (ChiCTR): "Pulmonary Artery Denervation in Patients with Pulmonary Artery Hypertention (The PADN-2 trial): a randomised controlled trial" dated Apr. 12, 2012, http://www.chictr.org/en/proj/ show.aspx?proj=2756 (4 pages).
Cruz, et al. Cardiopulmonary Effects Following Endoscopic Thoracic Sympathectomy . European Journal of Cardio-Thoracic Surgery, Published by Elsevier BV. (2009) 491-496.
European search report and opinion dated Nov. 18, 2015 for EP Application No. 13840133.
Farber, et al.Predicting outcomes in pulmonary arterial hypertension based on the 6-minute walk distance. J Heart Lung Transplant. Mar. 2015;34(3):362-8. doi: 10.1016/j.healun.2014.08.020. Epub Aug. 28, 2014.
Farber. Validation of the 6-minute walk in patients with pulmonary arterial hypertension: trying to fit a square PEG into a round hole? Circulation. Jul. 17, 2012;126(3):258-60. doi: 10.1161/CIRCULATIONAHA.112.118547. Epub Jun. 13, 2012.
Flues, et al. Cardiac and pulmonary arterial remodeling after sinoaortic denervation in normotensive rats. Auton Neurosci. Jan. 26, 2012;166(1-2):47-53. doi: 10.1016/j.autneu.2011.10.005. Epub Nov. 13, 2011.
Fritz, et al. Baseline and follow-up 6-min walk distance and brain natriuretic peptide predict 2-year mortality in pulmonary arterial hypertension. Chest. Feb. 1, 2013;143(2):315-23.
Frost, et al.Evaluation of the predictive value of a clinical worsening definition using 2-year outcomes in patients with pulmonary arterial hypertension: a REVEAL Registry analysis. Chest. Nov. 2013;144(5):1521-9. doi: 10.1378/chest. 12-3023.
Galie, et al. Guidelines for the diagnosis and treatment of pulmonary hypertension: the Task Force for the Diagnosis and Treatment of Pulmonary Hypertension of the European Society of Cardiology (ESC) and the European Respiratory Society (ERS), endorsed by the International Society of Heart and Lung Transplantation (ISHLT). Eur Heart J. Oct. 2009;30(20):2493-537. doi: 10.1093/eurheartj/ehp297. Epub Aug. 27, 2009.
Galie, et al. New treatment strategies for pulmonary arterial hypertension: hopes or hypes? J Am Coll Cardiol. Sep. 17, 2013;62(12):1101-2. doi: 10.1016/j.jacc.2013.06.032. Epub Jul. 10, 2013.
Galie, et al.A meta-analysis of randomized controlled trials in pulmonary arterial hypertension. Eur Heart J. Feb. 2009;30(4):394-403. doi: 10.1093/eurheartj/ehp022. Epub Jan. 20, 2009.
Galie, et al.Tadalafil therapy for pulmonary arterial hypertension. Circulation. Jun. 9, 2009;119(22):2894-903. doi: 10.1161/CIRCULATIONAHA.108.839274. Epub May 26, 2009.
Garutti, et al. Surgical upper thoracic sympathectomy reduces arterial oxygenation during one-lung ventilation. J Cardiothorac Vasc Anesth. Oct. 2005;19(5):703-4.
Hiremath, et al. Exercise improvement and plasma biomarker changes with intravenous treprostinil therapy for pulmonary arterial hypertension: a placebo-controlled trial. J Heart Lung Transplant. Feb. 2010;29(2):137-49. doi: 10.1016/j.healun.2009.09.005.

Humbert, et al. Survival in patients with idiopathic, familial, and anorexigen-associated pulmonary arterial hypertension in the modern management era. Circulation. Jul. 13, 2010;122(2):156-63. doi: 10.1161/CIRCULATIONAHA.109.911818. Epub Jun. 28, 2010.
International search report and written opinion dated Aug. 22, 2013 for PCT/CN2013/073338.
International search report and written opinion dated Nov. 23, 2015 for PCT/US2015/039930.
Juratsch, et al. Experimental pulmonary hypertension produced by surgical and chemical denervation of the pulmonary vasculature. Chest. Apr. 1980;77(4):525-30.
Lang, et al. Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology. J Am Soc Echocardiogr. Dec. 2005;18(12):1440-63.
Mclaughlin, et al. End points and clinical trial design in pulmonary arterial hypertension. J Am Coll Cardiol. Jun. 30, 2009;54(1 Suppl):S97-107. doi: 10.1016/j.jacc.2009.04.007.
Mclaughlin, et al. Prognosis of pulmonary arterial hypertension: ACCP evidence-based clinical practice guidelines. Chest. Jul. 2004;126(1 Suppl):78S-92S.
Mclaughlin, et al. Randomized study of adding inhaled iloprost to existing bosentan in pulmonary arterial hypertension. Am J Respir Crit Care Med. Dec. 1, 2006;174(11):1257-63. Epub Aug. 31, 2006.
Mereles, et al. Exercise and respiratory training improve exercise capacity and quality of life in patients with severe chronic pulmonary hypertension. Circulation. Oct. 3, 2006;114(14):1482-9. Epub Sep. 18, 2006.
Naeije, et al. Pulmonary vascular responses to surgical chemodenervation and chemical sympathectomy in dogs. J Appl Physiol (1985). Jan. 1989;66(1):42-50.
Notice of allowance dated Aug. 16, 2016 for U.S. Appl. No. 14/672,021.
Odero, et al. Left cardiac sympathetic denervation for the prevention of life-threatening arrhythmias: the surgical supraclavicular approach to cervicothoracic sympathectomy. Heart Rhythm. Aug. 2010;7(8):1161-5. doi: 10.1016/j.hrthm.2010.03.046. Epub Jun. 9, 2010.
Office action dated Jan. 5, 2015 for U.S. Appl. No. 14/530,588.
Office action dated Jan. 21, 2016 for U.S. Appl. No. 14/672,021.
Office action dated Feb. 4, 2016 for U.S. Appl. No. 14/079,230.
Office action dated Feb. 26, 2016 for U.S. Appl. No. 14/672,013.
Office action dated Jul. 14, 2015 for U.S. Appl. No. 14/666,214.
Office action dated Jul. 31, 2015 for U.S. Appl. No. 14/530,588.
Office action dated Aug. 5, 2015 for U.S. Appl. No. 14/672,010.
Office action dated Sep. 15, 2015 for U.S. Appl. No. 14/672,021.
Office action dated Oct. 8, 2015 for U.S. Appl. No. 14/672,013.
Office action dated Oct. 28, 2015 for U.S. Appl. No. 14/666,214.
Office action dated Dec. 21, 2015 for U.S. Appl. No. 14/672,010.
Ommen, et al. Assessment of right atrial pressure with 2-dimensional and Doppler echocardiography: a simultaneous catheterization and echocardiographic study. Mayo Clin Proc. Jan. 2000;75(1):24-9.
Savarese, et al. Do changes of 6-minute walk distance predict clinical events in patients with pulmonary arterial hypertension? A meta-analysis of 22 randomized trials. J Am Coll Cardiol. Sep. 25, 2012;60(13):1192-201. doi: 10.1016/j.jacc.2012.01.083.
Tei, et al. Noninvasive Doppler-derived myocardial performance index: correlation with simultaneous measurements of cardiac catheterization measurements. J Am Soc Echocardiogr. Mar. 1997;10(2):169-78.
Zhou, et al. Pulmonary Artery Denervation Attenuates Pulmonary Arterial Remodeling in Dogs With Pulmonary Arterial Hypertension Induced by Dehydrogenized Monocrotaline. JACC Cardiovasc Interv. Dec. 28, 2015;8(15):2013-23. doi: 10.1016/j.jcin.2015.09.015.
Chinese application No. CN20131103141 filed Mar. 27, 2013 with English Translation.

\* cited by examiner

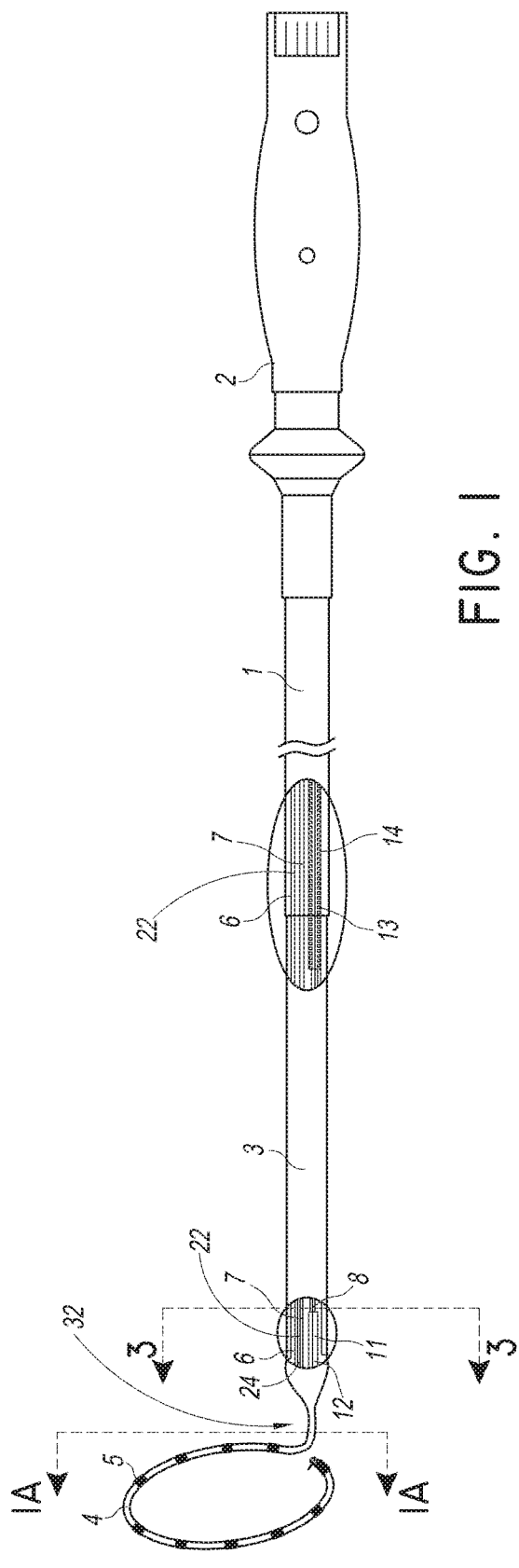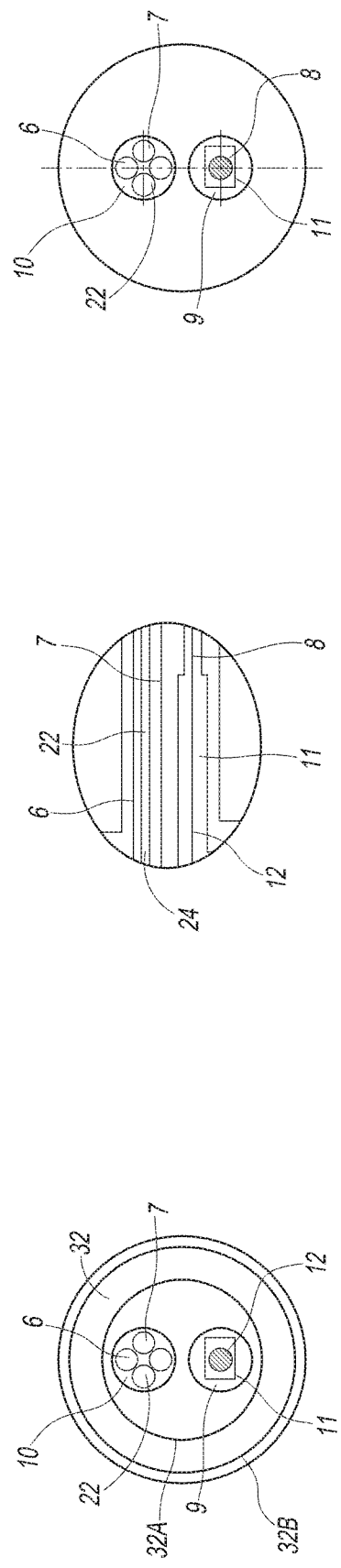

| Parameter | Systolic Pulmonary Artery Pressure (mmHg) | | | Mean Pulmonary Artery Pressure (mmHg) | | |
|---|---|---|---|---|---|---|
| | Before surgery | during surgery | Decline | Before surgery | during surgery | Decline |
| Parameter Status 1<br>Temperature <50°<br>Energy 8-10W<br>Ablation 120s | 96 | 94 | 2.1% | 56 | 54 | 3.6% |
| Parameter Status 2<br>Temperature 50°~60°<br>Energy 8-10W<br>Ablation 120s | 88 | 64 | 27.3% | 52 | 36 | 31% |
| Parameter Status 3<br>Temperature 40°~45°<br>Energy <8W<br>Ablation 120s | 86 | 86 | 0% | 54 | 53 | 1.9% |
| Parameter Status 4<br>Temperature 50°~60°<br>Energy 8-10W<br>Ablation 60s | 86 | 78 | 9.3% | 54 | 49 | 11.1% |

FIG. 14B

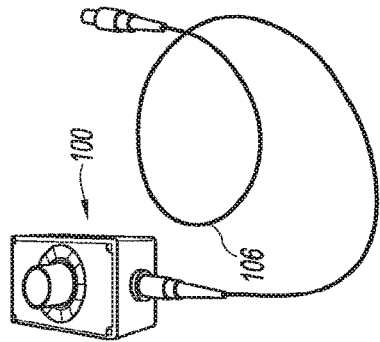
FIG. 15A
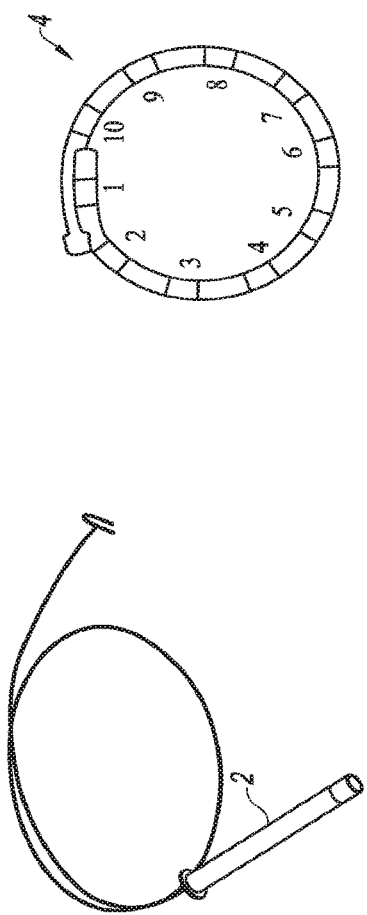
FIG. 15B
FIG. 15C
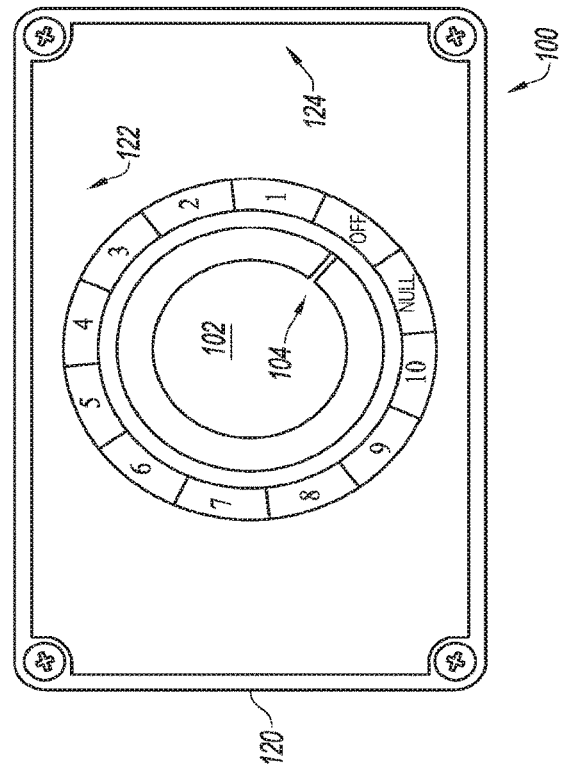
FIG. 15D
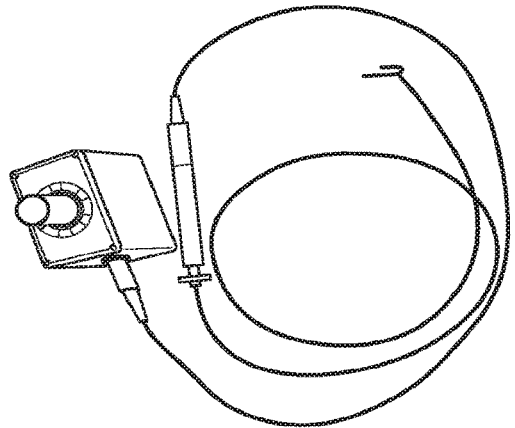
FIG. 15E

MULTI-POLE SYNCHRONOUS PULMONARY ARTERY RADIOFREQUENCY ABLATION CATHETER

CROSS-REFERENCE TO RELATED APPLICATIONS

This application is a continuation of U.S. patent application Ser. No. 14/530,588, filed Oct. 31, 2014, which is a continuation of U.S. patent application Ser. No. 14/079,230, filed Nov. 13, 2013, which claims priority to Chinese Application No. 201210453470.4, filed on Nov. 13, 2012 and Chinese Application No. 201310103141.1, filed on Mar. 27, 2013, the entire contents of each of which are hereby incorporated by reference.

BACKGROUND OF THE INVENTIONS

Field of the Inventions

The present inventions relate to medical devices for treatment of pulmonary hypertension in the pulmonary artery by de-sympathetic methods, for example, with multi-pole synchronous pulmonary artery radiofrequency ablation catheters, as well as methods for diagnosis and method of treating pulmonary hypertension.

Description of the Related Art

Pulmonary hypertension is to be an intractable diseases in the cardiovascular, respiratory, connective tissue, immune and rheumatic systems. Currently available clinical treatments of pulmonary hypertension are limited and therapy efficacy thereof is poor. Incidence of primary pulmonary hypertension is low but those secondary to pulmonary interstitial fibrosis, connective tissue disease, portal hypertension, chronic pulmonary artery embolism and left heart system disorder are common, with five-year mortality rate up to 30%. Therefore, prevention and treatment for pulmonary hypertension is of great significance.

In recent years, new targeted drugs have emerged based on the research into the pathogenesis of pulmonary hypertension. However, some of those drugs have serious limitations including many side effects, inappropriate dosage form, expensive cost and unreliable efficacy, and thus many have not been widely applied in clinical treatment.

SUMMARY OF THE INVENTIONS

An aspect of at least one of the inventions disclosed herein includes the realization, supported by experimental data which demonstrates, that pulmonary hypertension is associated with hyper sympathetic activity in pulmonary artery and hyperactive baroreceptor. Blocking the sympathetic nerves in the pulmonary artery or permanently damaging the baroreceptor structure and function thereof can decrease the pulmonary artery pressure, which can provide more successful treatments of pulmonary hypertension.

Some of the embodiments disclosed herein provide a multi-pole synchronous pulmonary artery radiofrequency ablation catheter for treatment of pulmonary hypertension in the pulmonary artery by a de-sympathetic method. In some embodiments, the catheter only heats the adherent tissue rather than the blood. Additionally, in some embodiments, the catheter can be configured to provide cold saline perfusion at or near the ablation site to protect the vascular intima. Some of the embodiments can also provide advantages of simple operation, short operation time and controllable, precise ablation.

In some embodiments, a multi-pole synchronous pulmonary artery radiofrequency ablation catheter can comprise a control handle, a catheter body and an annular ring. The control handle can be provided with an adjustment apparatus. The catheter body can be hollow and can include a cavity. One or a plurality of lead wires, one or more temperature sensing wires and one or more pull wires can be arranged in the cavity. One end of the catheter body can be flexible. The flexible end can be connected to an annular ring and the other end of the catheter body can be connected to the control handle. One end of the pull wire can be connected to the flexible end and the other end of the pull wire can be connected to the adjustment apparatus. Tension in the pull wire can be adjusted through the adjustment apparatus to achieve shape control, such as curvature control, of the flexible end. A shape memory wire can be arranged in the annular ring. One end of the shape memory wire can extend to the end of the annular ring and the other end of the shape memory wire can pass through the root of the annular ring and can be fixed on the flexible end of the catheter body. The annular ring can be provided with an electrode group with each electrode connected to the one or more lead wires and the one or more temperature sensing wires. The lead wire(s) and the temperature sensing wire(s) extend through the catheter body and are electrically connected to the control handle.

An infusion tube can be arranged in the cavity of the catheter body and a through hole can be arranged on one or more of the electrodes. The infusion tube can be connected to the electrodes through the annular ring. The transfused fluid flows out from the through hole and thus can be used for cooling purposes during ablation procedures.

The electrodes on the annular ring can be made of a material selected from the group consisted of platinum-iridium alloy, gold, stainless steel and nickel alloy, with the number in the range of 3-30 electrodes, a diameter in the range of 1.3-2.0 mm, a length in the range of 1.2-4 mm and an edge space between adjacent electrodes in the range of 0.5-10 mm.

The flexible end of the catheter body can be provided with a counterbore, an inner diameter of the counterbore can be sized to fit an outer diameter of the root of the annular ring, and thus the root of the annular ring can be inserted and fixed into the counterbore.

The flexible end of the catheter body is provided with a groove in which a connector is arranged, one end of the connector is connected to the pull wire and the other end of the connector is connected to the shape memory wire.

The material of the shape memory wire in the annular ring can be a shape memory alloy selected from the group consisted of nickel titanium alloy, stainless steel or titanium, with a diameter of 0.25-0.5 mm. The diameter of the annular ring can be 12-40 mm. For example, the annular ring can be configured so as to be biased toward a circumferential shape, having a desired diameter (e.g., in the range of 12-40 mm), for example, with the use of a memory shape material. Preferably, 10 electrodes are arranged on the annular ring. The width of naked section of the electrode is 0.75 mm, and the space there between is 5 mm.

The flexible end can be made of medical polymer materials with a length in the range of 30-80 mm. The connection can be achieved by a UV-curing adhesive. The joint between the flexible end and the annular ring can be sealed.

The pull wire is made of stainless steel or nickel-titanium alloy. The outside of pull wire is provided with a spring coil, and the outside of the spring coil is provided with a spring sleeve made of polyimide material.

In some embodiments, the catheter can be packaged into a kit including a plurality of different annular rings that are biased to different diameters. In some embodiments, where the annular rings, flexible bodies, and handles are permanently connected together, a kit can include a plurality of different catheters, each having handles and flexible bodies, but differently sized annular rings.

In some embodiments and/or methods of use, the catheter can heat, with radiofrequency energy, the tissue in direct contact with the electrode and avoid heating blood. Additionally, the catheter can provide advantages of simple operation, short operation time and controllable precise ablation. The catheter body can be preferably made of a polymer material, which is a poor heat conductor, so that it can avoid transmitting the heat when heating the electrodes to the flowing blood contacting the catheter body, thereby effectively avoid heating the blood.

Furthermore, the shape or curvature of the flexible end can be adjusted by operating the adjustment apparatus, which allows the operator to control the handle with one hand, so as to adjust the curvature of the flexible end easily for purposes of placement of the annular ring and the electrodes. As such, after achieving the desired placement, the electrodes on the annular ring can be pressed against the pulmonary artery and achieve ablation of pulmonary artery intima. During application of the radiofrequency current, the electrodes can produce high local temperature and cause severe damage on the vascular intima.

Thus, in some embodiments, the catheter can be configured to provide cold saline perfusion to cool down the local temperature. When the electrodes receive the current, the saline is automatically and uniformly diffused through the through holes, which can provide beneficial cooling, for example, decreasing the local temperature to be below 60° C., thereby protecting the vascular intima.

BRIEF DESCRIPTION OF THE DRAWINGS

FIG. 1 is a schematic structural diagram of an embodiment of a catheter in accordance with an embodiment;

FIG. 1A is a schematic sectional view taken along line 1A-1A of FIG. 1;

FIG. 2 is a partially enlarged view of Part B identified in FIG. 1;

FIG. 3 is schematic sectional view taken along line 3-3 of FIG. 1;

FIG. 14B is a table showing reductions in PAP resulting from the use of different ablation operating parameters;

FIG. 15A is a perspective view of a catheter device that can be used to perform pulmonary denervation;

FIG. 15B is an enlarged end view of a distal end of the catheter of FIG. 15A with indicia indicating positions of ten (10) RF electrodes;

FIG. 15C is a perspective view of a controller that can be used for controlling the catheter of FIG. 15A during an ablation procedure;

FIG. 15D is a top plan view of the controller of FIG. 15C;

FIG. 15E is a perspective view of the controller connected to the catheter device of FIG. 15A;

FIG. 16D illustrates a position used for ablation and arterial denervation of the left pulmonary artery of the patient;

Detailed Description of the Preferred Embodiment

Figure 4:
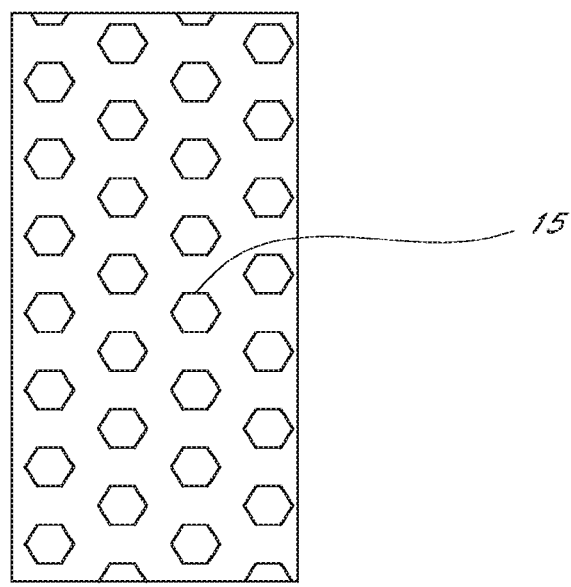
FIG. 4 is a schematic structural view of an optional outer surface of an electrode that can be used with the catheter of FIG. 1.

The following examples further illustrate embodiments of the present inventions, but should not be considered as to limit the present inventions. Without departing from the spirit and essence of the present inventions, modification or replacement of the method, steps or conditions of the embodiments disclosed below still falls in the scope of the present inventions.

If not otherwise specified, the technical means used in the embodiments are conventional means well known by a person skilled in the art.

Example 1

Through the example below and with reference to FIGS. 1-3, some of the technical solutions that can be achieved by various embodiments are further described below.

In some embodiments, a multi-pole synchronous pulmonary artery radiofrequency ablation catheter for de-sympathetic in the pulmonary artery can include a catheter body 1 that has a distal end and a proximal end. The distal end can be provided with a flexible end 3 and the proximal end can be provided with a control handle 2. A pull wire can extend in the catheter body.

Preferably, the catheter body can be made of a polymer material, which is a poor heat conductor, so that it can avoid transmitting or reduce the amount of heat transferred from the electrodes to the flowing blood contacting the catheter body, and thereby can better prevent the electrode from heating the blood flow.

The flexible end 3 can include a proximal end and a distal end. An annular ring 4 can be arranged on the distal end. The flexible end 3 can be soft relative to the rest of the catheter body. The annular ring 4 can be provided with a plurality of electrodes 5, wherein each electrode 5 can be configured to sense or extract neural electrical signals, sense temperature and conduct ablation. Each of the electrodes can be connected to lead wires and temperature sensing wires, which extend through the catheter body to the control handle, thus is electrically connected to the control handle. One or more temperature sensing wires can be embedded under each electrode for precise monitoring of the temperature during ablation. Additionally, in some embodiments, the temperature sensing wires can be connected to a thermocouple connected to an inner facing side of the electrodes 5, or can include integrated thermocouples. Other configurations can also be used.

A shape memory wire can be arranged in the annular ring 4, and a distal end of the shape memory wire can extend to the distal end of the annular ring 4. The proximal end of the shape memory wire can be fixed to the distal end of the flexible end. The shape memory wire in the annular ring 4 can be preferably made of various shape memory alloys such as nickel-titanium alloy, stainless steel or titanium, with a diameter in the range of 0.25-0.5 mm.

The diameter of the annular ring is in the range of 12-40 mm. For example, the shape memory wire can be configured to bias the annular ring 4 to a desired diameter, such as in the range of 12-40 mm. Additionally, in some embodiments, the pull wire can be used the change or adjust the diameter of the annular ring 4 through a range of diameters including 12-40 mm or other ranges.

The length of the flexible end can be in the range of 30-80 mm, and can be made of medical polymer materials such as fluorine, polyesters, polyurethane, polyamide and polyimide. A counterbore can be arranged on the distal end of the flexible end, the proximal end of the annular ring can be fixed in the counterbore, wherein the proximal end of the annular ring is a ground thin end.

A pull wire can be embedded in the catheter body, and one end of the pull wire can be fixed to the control handle. The curvature of the flexible end can be controlled by operating the control handle. For example, one end of the pull wire can be fixed to a control button on the handle and the curvature of the flexible end can be controlled by operating the button. This allows the operator to control the handle with one hand and adjust the curvature of the flexible end easily, so that the electrodes 5 on the annular ring 4 can be pressed into contract with the pulmonary artery and achieve acceptable ablation of pulmonary artery intima.

Furthermore, a counterbore can be made on the distal end of the flexible end 3, and its depth can be set according to actual needs, preferably with a depth in the range of 2-8 mm. The proximal end of the annular ring 4 can be a ground thin end, and an outer diameter of the ground thin end fits an inner diameter of the counterbore. The ground-thin end can be inserted into the flexible end 3 and can be fixed to the distal end of the flexible end 3 by bonding, welding or other suitable means, preferably by UV-curing adhesive. The excess glue may be used to seal the distal end of the flexible end 3 and the proximal end of the annular ring 4.

FIG. 1 shows a schematic structural diagram of multi-pole synchronous pulmonary artery radiofrequency ablation catheter. The annular ring 4 can be arranged at the distal end of the flexible end 3. The annular ring 4 can be an annular structure, the radius of the annular ring 4 can be effected with shape memory wire.

The annular ring 4 can be provided with a plurality of electrodes 5. Each electrode 5 can be configured to extract or detect neural electrical signals, sense the temperature and conduct ablation. The number of electrodes 5 can vary from the range of 3 to 30, preferably 5 to 20. The electrodes 5 are made of platinum-iridium alloy, gold, stainless steel or nickel alloy. The electrode diameter can be generally 1.3-2.0 mm, and the length of the electrode 5 can be generally in the range of 1.2-4 mm, more suitably 2-3.5 mm. Edge space between the adjacent electrodes suitably can be in the range of 0.5-10 mm, more suitably 1-5 mm.

The pull wire 8 can be preferably made of stainless steel or nickel-titanium. As shown in FIG. 2 and FIG. 3, the distal end of the pull wire 8 extends through a hollow cavity 9 to the proximal end of the annular ring 4, and can be fixed to the distal end of the flexible end 3. The method used for fixing the pull wire 8 to the distal end of the flexible end 3 can be any known method in the prior art.

Optionally, a groove can be arranged on the distal end of the flexible end 3, and a connector 11 can be arranged in the groove. One end of the connector 11 can be connected to the pull wire 8 and the other end of the connector 11 can be connected to the shape memory wire 12. The connector 3 can be fixed to the distal end of the flexible end 3 by injecting glue such as UV-curing adhesive into the groove.

A segment of pull wire 8 extends in the flexible end 3 and a segment of pull wire 8 extends in the catheter body 1. The pull wire can be preferably jacketed with a coil spring 13, and the coil spring 13 can be jacketed with a spring sleeve 14. The spring sleeve 14 may be made of any suitable material, preferably a polyimide material.

The proximal end of the pull wire 8 can be fixed on or in the control handle 2, which can be provided with an adjustment apparatus, and the adjustment apparatus can be configured to adjust the curvature or the diameter of the annualar ring 4.

Lead wire 6, as shown in FIGS. 2 and 3, extends through the lead wire cavity 10 to the lead wire cavity of the annular ring 4. The distal end of the lead wire 6 can be connected to electrode 5. The distal end of the lead wire 6 can be fixed to electrode 5 by welding. In some embodiments, the catheter includes one lead wire 6 for each of the electrodes 5.

The distal end of the temperature sensing wire 7 can be embedded under the electrode 5 and the distal end of the temperature sensing wire 7 can be fixed on electrode 5 by bonding, welding or other suitable means. The temperature sensing wire 7 can extend into the catheter body 1 in the lead wire cavity 10 of the flexible end 3 and then extend out from the control handle 2 and can be connected to a temperature control device. In some embodiments, the catheter includes one temperature sensing wire 7 for each of the electrodes 5.

When using the catheter, the pull wire 8 can be operated through the control handle 2 in order to deflect the flexible end 3, thereby providing enhanced control for the user when positioning the annular ring 4 in a desired location, such as an orifice of the pulmonary artery. Then, with the electrodes 5 fully contacting the pulmonary artery. At this time, the electrodes 5 can be energized for performing ablation on pulmonary artery intima.

The multi-electrode design according to the some embodiments, can improve the efficacy and safety of ablation, achieve signal analysis and preferably simultaneous ablation by a plurality of electrodes. This can also improve target accuracy, achieve timely judgment of ablation effect and save operation time. For example, with the annular ring 4 in a desired location, the electrodes can be individually activated to perform ablation at selected sites. This can be a benefit because in some methods of treatment described below, ablation can be performed at selected sites, less than the entire circumferential surface of certain anatomy.

Example 2

A multi-pole synchronous pulmonary artery radiofrequency ablation catheter comprises a control handle 2, a catheter body 1, and an annular ring 4. The control handle 2 can be provided with an adjustment apparatus, the catheter body 1 can be hollow, and a cavity can be arranged in the catheter body 1. One or more lead wires 6, temperature sensing wires 7 and a pull wire 8 can be arranged in cavity.

One end of catheter body can be flexible, and the flexible end 3 can be connected to the annular ring 4. The other end of the catheter body can be connected to the control handle 2. One end of the pull wire 8 can be connected to the flexible end 3, and the other end of the pull wire 8 can be connected to the adjustment apparatus of the control handle, the adjustment apparatus adjusts the tension of the pull wire 3 to control the curvature of the flexible end. This allows the operator to control the handle with one hand and adjust the curvature of the flexible end 3 easily. Thereby the electrodes 5 of the annular ring 4 can be pressed against to better contact an inner surface of a desired anatomy, such as a pulmonary artery, so as to enhance ablation of pulmonary artery intima.

A shape memory wire 12 can be arranged in the annular ring 4. One end of the shape memory wire 12 can extend to the end of the annular ring 4, and the other end of the shape memory wire 12 goes through the root of the annular ring 4 and can be fixed on the flexible end 3 of the catheter body.

The annular ring 4 can also be provided with an electrode group. Each electrode 5 can be connected to a lead wire 6 and a temperature sensing wire 7 and can be configured to extract or detect the nerve electrical signals, sense the temperature and conduct ablation. The lead wires 6 and temperature sensing wires 7 can extend through the catheter body 1 and can be electrically connected to the control handle 2. The control handle 2 can be connected to an external temperature control device.

The annular ring electrodes 5 can be made of a material selected from the group consisted of platinum-iridium alloy, gold, stainless steel and nickel alloy material, with the number in the range of 3-30, a diameter in the range of 1.3-2.0 mm, a length in the range of 1.2-4 mm and an edge space between adjacent electrodes in the range of 0.5-10 mm.

The flexible end 3 of the catheter body can have a counterbore 32 having an inner diameter 32A and an outer diameter 32B. An outer diameter of the root of the annular ring 4 can fit the inner diameter 32A of the counterbore 32. The root of the annular ring 4 can be inserted into the counterbore 32 and fixed.

The flexible end 3 of the catheter body can be provided with a groove. A connector 11 can be arranged in the groove. One end of the connector can be connected to the pull wire 8 and the other end of the connector can be connected to the shape memory wire 12.

The shape memory wire can be made of shape memory alloy such as nickel titanium alloy, stainless steel or titanium, with a diameter in the range of 0.25-0.5 mm. The diameter of the annular ring 4 can be in the range of 12-40 mm. Preferably, 10 electrodes are arranged on the annular ring, and the width of naked (exposed) side of electrodes can be 0.75 mm, and the space there between can be 5 mm.

The flexible end 3 of the catheter body can be made of medical polymer materials such as fluorine, polyesters, polyurethane, polyamide and polyimide, with a length in the range of 30 mm to 80 mm.

The connection can be via UV-curing adhesive. The joint between the flexible end of the catheter body and the annular ring can be sealed. The pull wire can 8 be made of stainless steel or nickel-titanium alloy. The pull wire 8 can be jacketed with a coil spring 13, and the coil spring 13 can be jacketed with a spring sleeve 14 made of polyimide material.

Example 3

Example 3 is similar to Example 1 and Example 2, and the differences can include an infusion tube 22 arranged in the catheter body, a group of evenly distributed through holes 15 (FIG. 4) arranged on one or more of the electrodes 5, with a bore diameter of 1 μm. One end of the infusion tube 22 can be connected to the electrodes 5 through the annular ring 4 such that fluid diffuses out from the through holes 15 on each of the electrodes 5. For example, the annular ring 4 can include or define at least one lumen 24 extending between a proximal end of the annular ring 4 and to the through holes 15 so as to form a closed fluidic connection. In such embodiments, a distal end of the infusion tube 22 can be connected to the proximal end of the lumen in the annular ring 4. The other end of the infusion tube 22 can be connected to a transfusion system, such as a constant-flux pump or other known pumps.

When electrodes 5 generates current, the liquid automatically diffuses from the through holes 15. The transfused liquid can be saline. The cold saline (4° C.) perfusion can help decrease local temperature. When the electrode generates current, the saline can automatically diffuse from the through holes 15, and thus can allow the local temperature to be controlled to a desired temperature, such as to below 60° C. and thereby protect the vascular intima.

Figure 5:
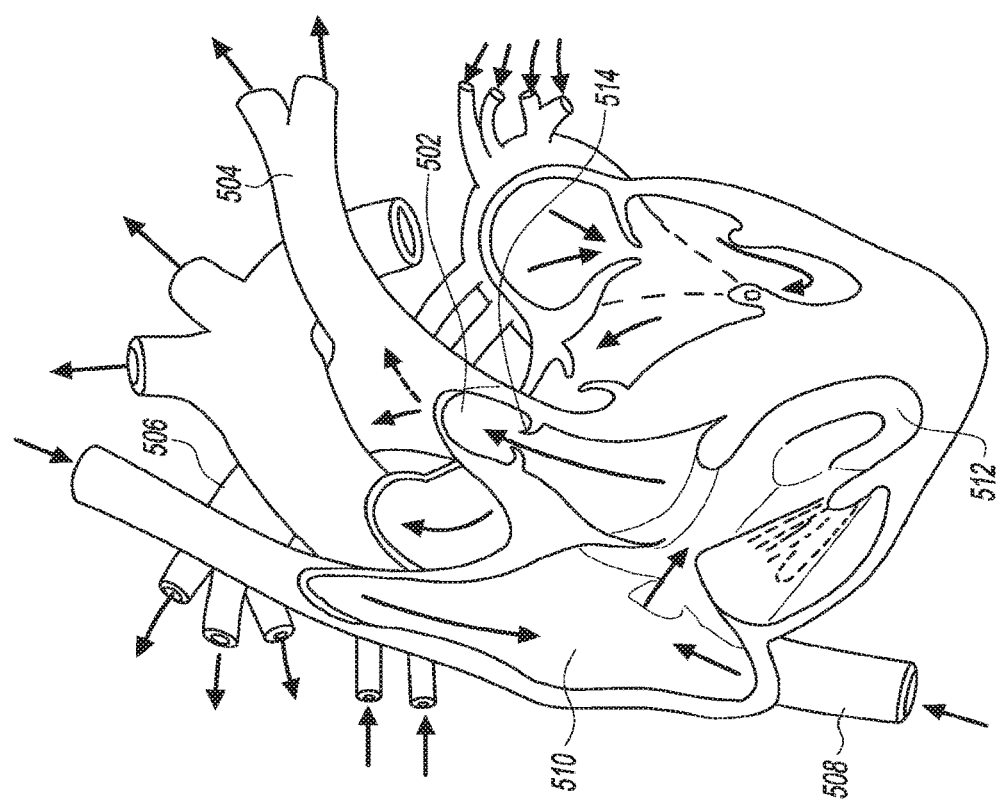
FIG. 5 is a front elevational and partial sectional view of a human heart.

FIG. 5 is a schematic diagram of a human heart and surrounding vasculature, which can be an environment in which the catheter of FIGS. 1-4 can be used to perform ablation treatments such as, for example, but without limitation, denervation of the pulmonary artery. In some methods of treatment, access to the inner walls of the main pulmonary artery 502 as well as the left pulmonary artery 504 and right pulmonary artery 506 can be achieved by passing a catheter, using well known techniques, into a femoral vein, upwardly into the inferior vena cava 508 (lower left hand corner of FIG. 5). The catheter can then be pushed upwards into the right atrium 510, down into the right ventricle 512, then up through the pulmonary semilunar valve 514 into the trunk of the main pulmonary artery. As used herein, the term main pulmonary artery (MPA) 502 includes the proximal end of the main pulmonary artery which is the furthest upstream end of the main pulmonary artery 502, at the pulmonary semilunar valve 514, up to the bifurcation of the main pulmonary artery. The distal portion of the MPA 502 includes the portions of the MPA 502 near the bifurcation of the MPA 502 into the left and right pulmonary arteries (LPA 504, RPA 506).

Similarly, the proximal ends of the RPA 506 and LPA 504 are those ends of the LPA 504 and RPA 506 which are adjacent and connected to the distal end of the MPA 502. The distal direction along the LPA 504 and RPA 506 would be the downstream direction of blood flow through the LPA 504 and RPA 506 toward the left and right lungs, respectively.

Thus, using well known techniques, a catheter can be used to provide access to the proximal and distal portions of the MPA 502 as well as the proximal and distal portions of the LPA 504 and RPA 506.

Figure 6:
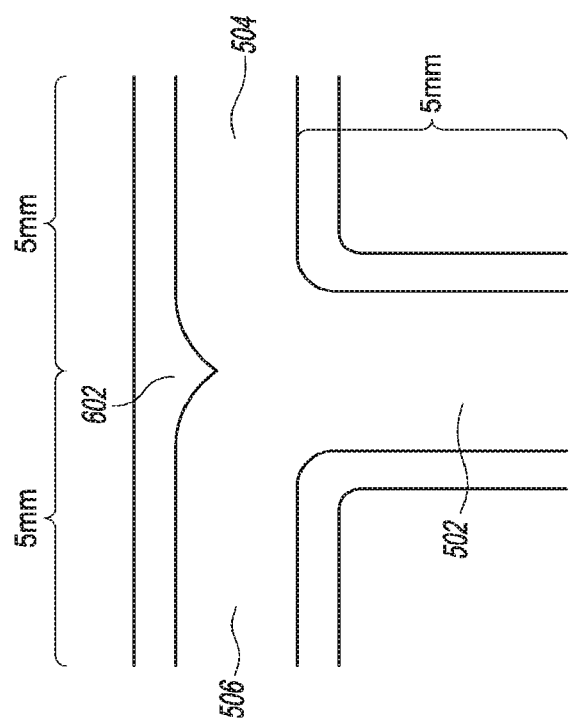
FIG. 6 is a schematic sectional diagram of a pulmonary artery trunk including a distal portion of a main pulmonary artery and the proximal portions of the left and right pulmonary arteries.

FIG. 6 is a schematic diagram of the "trunk" of the pulmonary artery. As used herein, the "trunk" of the MPA 502 is intended to include at least the distal portion of the MPA and the proximal portions of the LPA 504 and RPA 506. FIG. 6 also includes a schematic representation of a carina 602 at the branch of the LPA 504 and RPA 506 from the MPA 502.

As described below, an aspect of at least some of the inventions disclosed herein includes the realization that the trunk of the pulmonary artery of certain animals, including canine and humans, can include concentrated bundles of sympathetic nerves extending from the MPA 502 into the LPA 504 and RPA 506. For example, it has been discovered that there are higher concentrations of sympathetic nerves on the anterior sides of the MPA 502 and in particular, in the vicinity of the distal portion of the MPA 502. Additionally, it has been discovered that the sympathetic nerves bifurcate from this area of higher concentration into the anterior side of the proximal portions of the LPA 504 and RPA 506. In the area of these proximal portions, it has also been discovered that higher concentrations of the sympathetic nerves extend upwardly and toward the posterior side of the LPA 504 and RPA 506.

Thus, in accordance with some of the inventions disclosed herein, ablation is performed in the distal portion of the MPA 502 and the proximal portions of the LPA 504 and RPA 506. In some embodiments ablation is preferentially performed on the anterior side of the inner walls of these structures. In some embodiments, ablation is performed preferentially on the anterior side of the proximal portion of the MPA 502 and on the anterior side and an upper portion of the proximal portions of the LPA 504 and RPA 506, such as at approximately the upper conjunctive site of the distal portion of the MPA 502 at the LPA 504 and RPA 506. As such, high success rates of sympathetic nerve denervation can be achieved as well as high success rates of reduction or elimination of the symptoms of pulmonary hypertension.

It is widely accepted that all vascular walls are regulated by sympathetical and parasympathetical nervous systems. Particularly, pulmonary vessels are known to be innervated by sensory nerve fibers. Previous studies have demonstrated that sympathetic noradrenergic innervation density along the pulmonary artery is highest at its proximal segments and then decreases toward the periphery, a typical finding that is different than arteries in other organs where highest innervation density is found at the level of the smallest arterioles. However, the conclusions of the above-noted study were based on procedures in which the identification of innervation in the pulmonary artery was mainly based on the stimulation of sympathetical nerves or equivalent methods, without direct evidence or other location of sympathetical nerve fibers. However, it has been discovered that some of the conclusions of the above-noted study are incorrect, through the use of techniques for identifying the presence and location of sympathetical nerves in the pulmonary artery using direct labeling techniques.

In particular, experimental procedures were approved by the Institutional Animal Care and Use Committees of the Nanjing Medical University and were performed in accordance with the National Guide for the Care and Use of Laboratory Animals. Mongolia dogs (n=6, weight 7.8±1.2 kg) were obtained from the Nanjing Experimental Center (Nanjing, China). All animals were housed in a single room at 24° C. on a 12 h-light/12 h-dark cycle with fresh food and water.

In this study, a dog was anesthetized with sodium pentobarbital (60 mg per kg, intraperitoneal injection). The chest was excised and opened carefully. The whole pulmonary artery was removed from the chest, with particular attention to avoid the injury of adventitia. In one dog, the pulmonary artery was longitudinally cut along the blood flow direction from the orifice of the main pulmonary artery (the proximal portion of the main pulmonary artery) toward the right and left branches. Then, a vernier focusing camera was used to take pictures in order to identify whether there is a visible difference in the surface of the pulmonary artery between different segments.

With regard to five other dogs, connective tissue was manually dissected away from the pulmonary artery using fine microdissection scissors, under the guidance of stereomicroscope. During this procedure, great care was taken to avoid stripping off the adventitia and possible damage to the perivascular nerves. Vessels were stored at −70° for further staining.

Frozen vessels were processed in paraffin wax and fixed in 4% paraformaldehyde for 30 minutes and then incubated at 0.5% Pontamine Sky Blue (Sigma-Aldrich, St. Louis, Mo.) in phosphate-buffered saline (PBS) for 30 minutes to reduce background fluorescence. This was followed by 1 hour at room temperature in a blocking solution of 4% normal goat serum/0.3% Triton X-100 in PBS, then overnight at 4° C. in blocking solution containing an affinity-purified polyclonal antibody against tyrosine hydroxylase (Temecula, Calif.). Vessel segments were then washed in PBS and incubated for 1 hour with secondary antibody (Invitrogen, Carlsbad, Calif.), washed again and positioned on a glass slide. Preparations remained immersed in PBS during image acquisition to maintain hydration and preserve vessel morphology.

Based on previous studies, the sympathetical nerves were thought to be mainly localized at the proximal segment of the pulmonary artery. Thus the distal segment (5 mm in length) of the main pulmonary artery and proximal 5 mm segments of the right and left branches were selected for investigation in the present study. FIG. 6 schematically illustrates, not to scale, a 5 mm segment of the distal portion of the MPA and 5 mm long proximal portions of the LPA and RPA.

Figure 8:
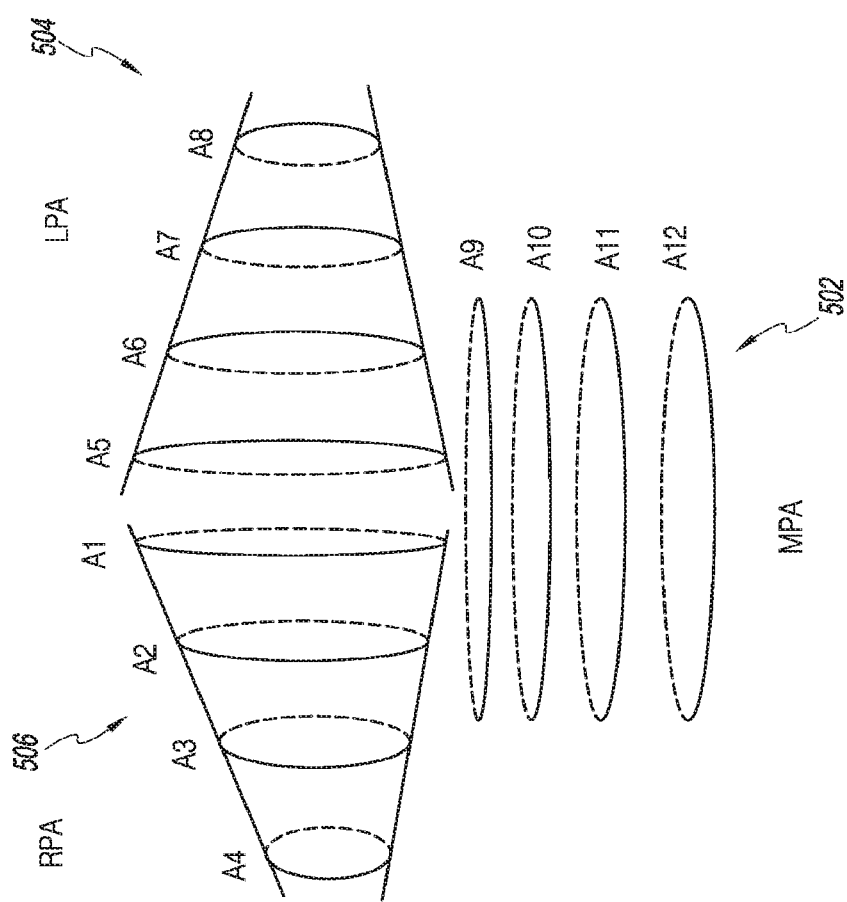
FIG. 8 is a schematic diagram of segmentations of dissected pulmonary arteries including the distal portion of the main pulmonary artery and the proximal portions of the left and right pulmonary arteries.
Figure 14A:
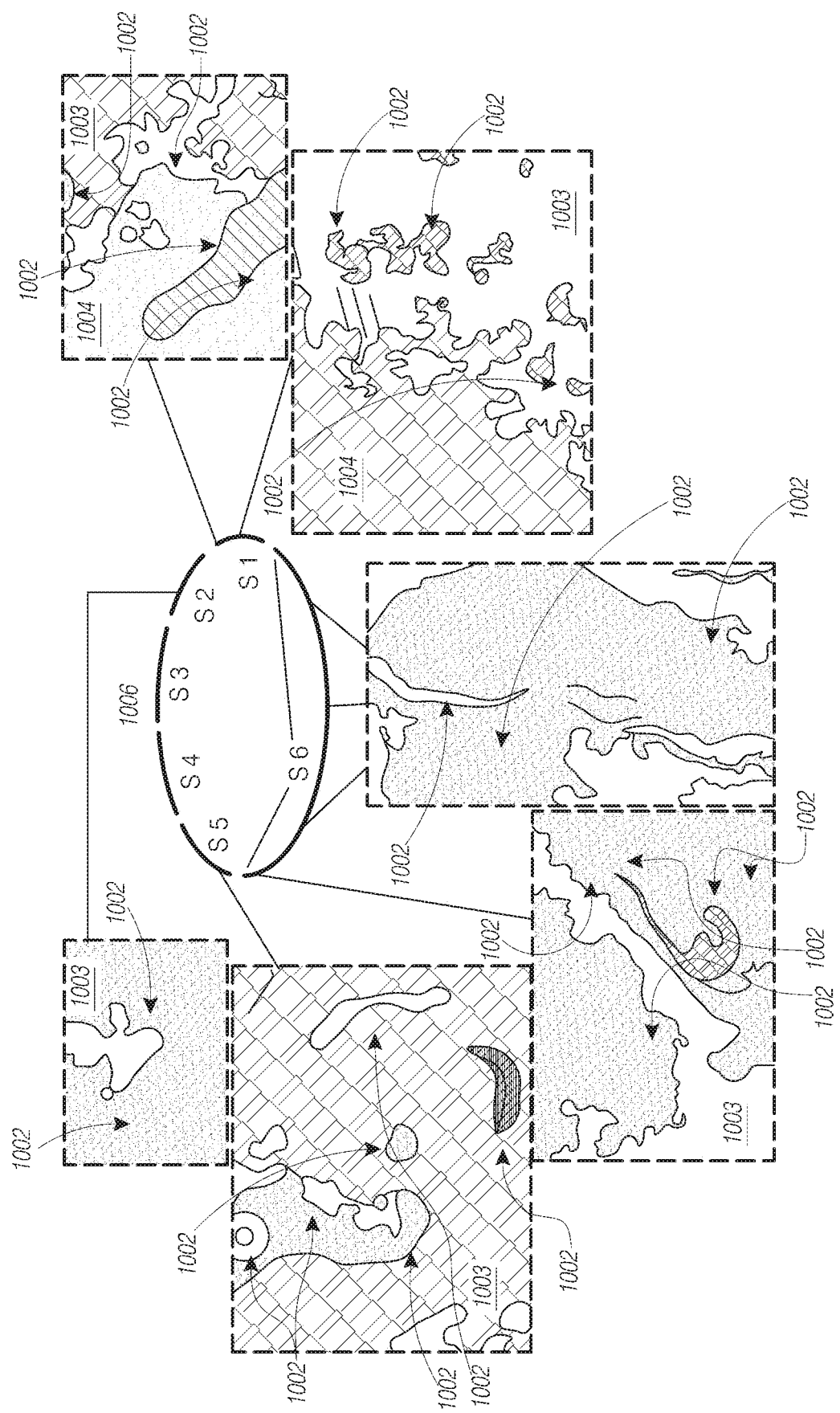
FIG. 14A is a diagram identifying the location corresponding to microscopy of six different locations on level A9 of the main pulmonary artery of FIG. 8.

Multiple transverse slices (2 μm of thickness) of the vessels were cut at 1.6 mm intervals, and are identified in the description set forth below in accordance with the labels of FIG. 8 (A1, A2, A3, A4, A5, A6, A7, A8, A9, A10, A11, A12). FIG. 14A is a diagram identifying the location corresponding to microscopy of six different locations on level A9 of the main pulmonary artery of FIG. 8 showing a posterior section 1006, adventitia 1003, and media 1004. Care was taken to keep the luminal morphology of slices consistent with the vessel contour, in order to precisely position the location of nerves. The slices were examined by a pathologist.

Images of each slices were recorded (magnification 40× to 200×) using stereomicroscope (Olympus), and the numbers of total sympathetical nerves bundles (SPNDs) per level were manually calculated. Then all images were input to Image Analysis Software (Image-proplus 5.0), to calculate the minor radius (μm), major radius (μm) and total surface area (TSA, $μm^2 \times 10^3$) area of axons.

Figure 7B:
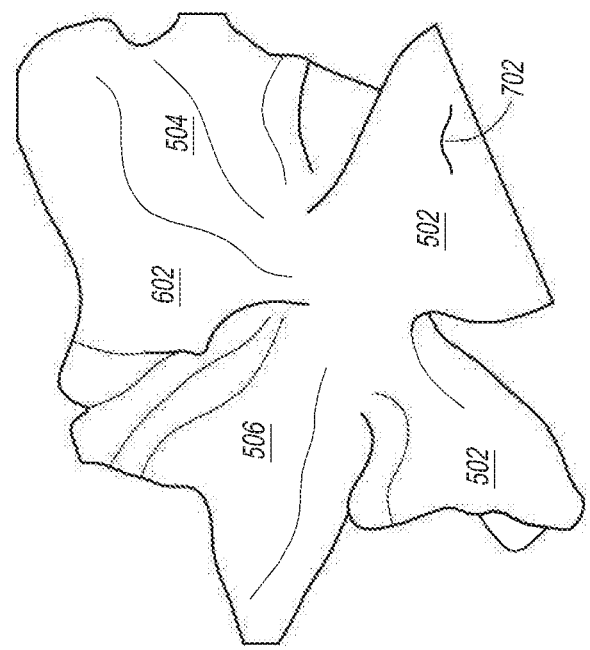
FIGS. 7A and 7B are diagrams of the inner surfaces of two canine pulmonary arteries that have been dissected and laid flat.
Figure 7A:
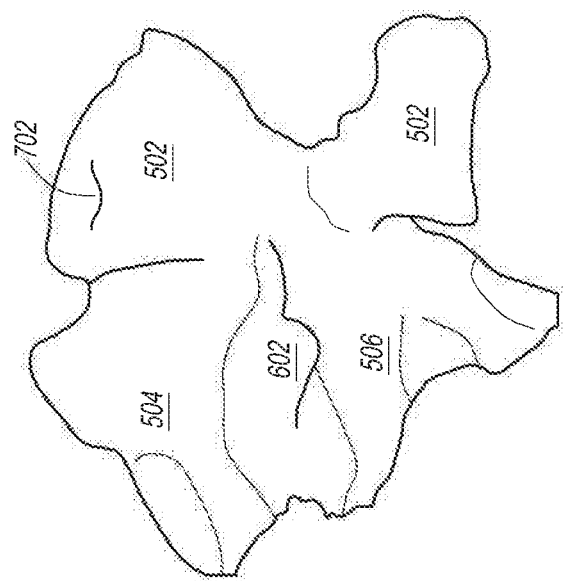

After the pulmonary artery was removed from the chest of the dog, the pulmonary artery was repeatedly cleaned with saline to clean away all blood on the surface of the vessel. Then the whole vessel was cut along the direction from the proximal portion of the main pulmonary artery up through the trunk and into the right and left branches. The above-noted diagrams (FIGS. 7A, 7B) showed that in the anterior wall of the main pulmonary artery, there was an obvious ridgy cystica 702 close to the orifice of the left pulmonary artery. The site of the ridgy cystica 702 felt rigid to the touch, compared to other areas of the pulmonary artery.

Figure 9C:
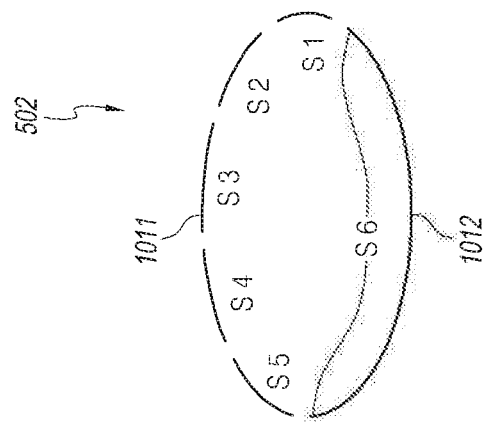
FIGS. 9A-9C are diagrams of three of the segmentations identified in FIG. 8.
Figure 9B:
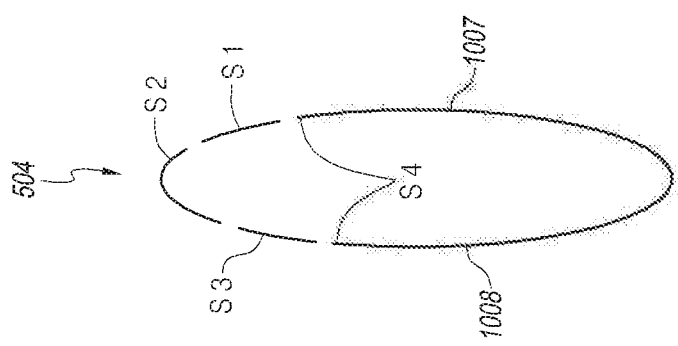
Figure 9A:
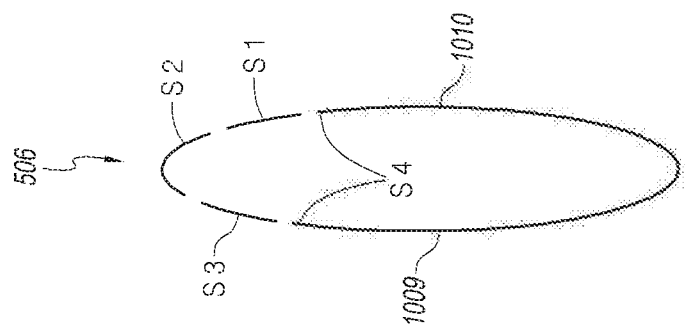

In the vicinity of the bifurcation portion of the pulmonary artery, segments 5-mm in length of the distal main pulmonary artery and the proximal portions of the right and left pulmonary arteries were studied. Four transverse slices (thickness 2 μm, 1.6-mm intervals) from each segment were prepared for analysis. Each slice ("level") was divided into 4 subsegments in the right and left pulmonary arteries (S1, S2, S3, S4 in FIGS. 9A-9C) and 6 subsegments in the main pulmonary artery along the counterclockwise direction (S1, S2, S3, S4, S5, S6 in FIGS. 9A-9C). FIG. 9A further shows an anterior wall 1009 and a posterior wall 1010. FIG. 9B further shows a posterior wall 1008 and an anterior wall 007. FIG. 9C further shows a posterior wall 1011 and an anterior wall 1013. FIGS. 10A-10D are enlargements of microscopy slides corresponding to the portions identified as S1-S4, respectively, of level A1 of the right pulmonary artery of FIGS. 9A-9C. FIGS. 10A-10D show adventitia 1003, 1004, and a lumen 1005.

Figure 10A:
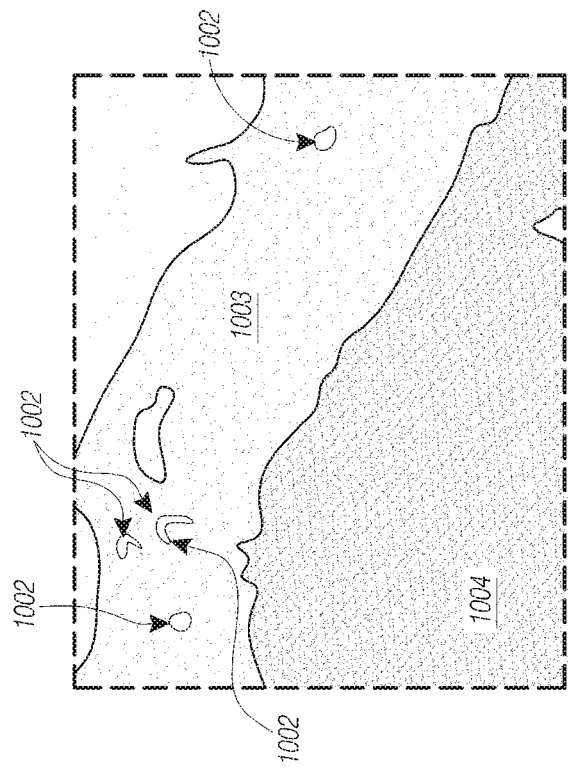
FIGS. 10A-10D are illustrations depicting enlargements of microscopy slides corresponding to the portions identified as S1-S4 of level A1 of the right pulmonary artery of FIG. 9A.
Figure 10B:
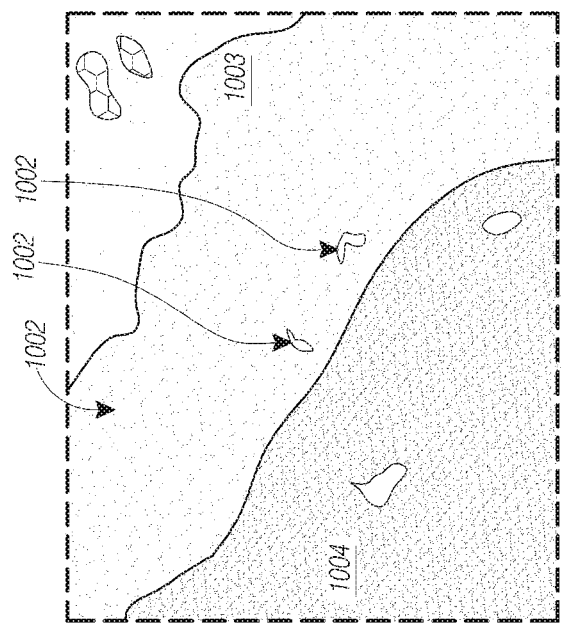
Figure 10D:
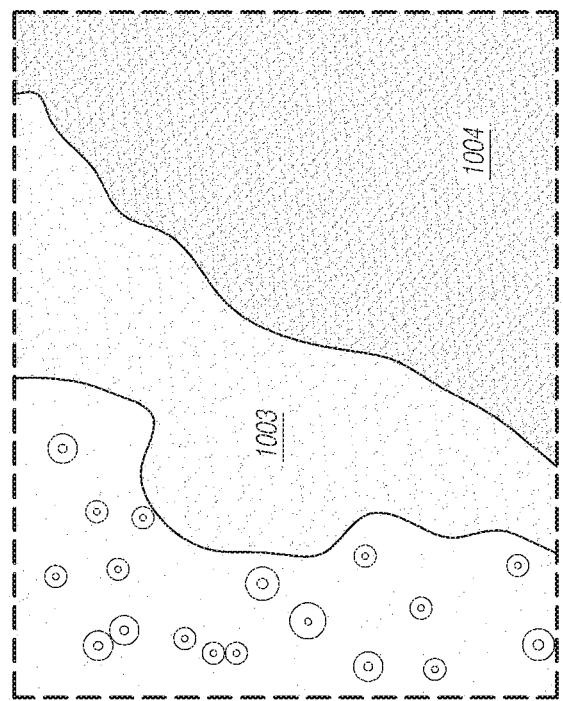
Figure 10C:
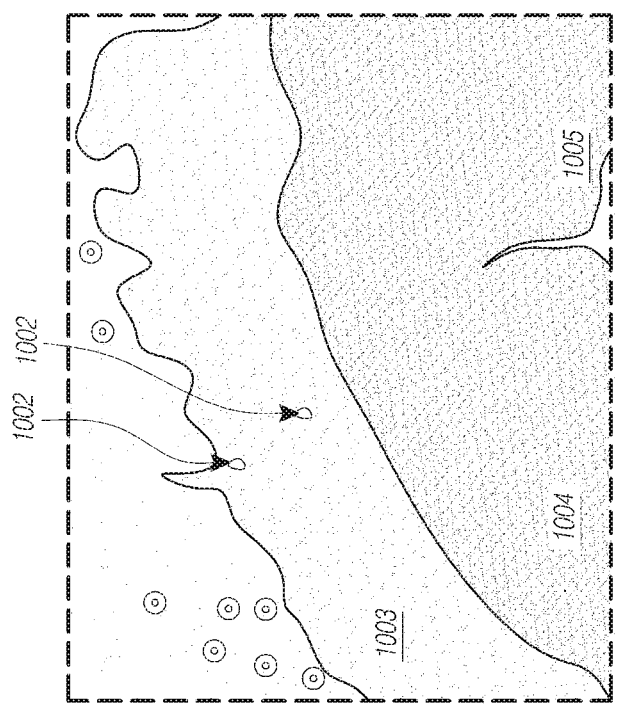
Figure 11:
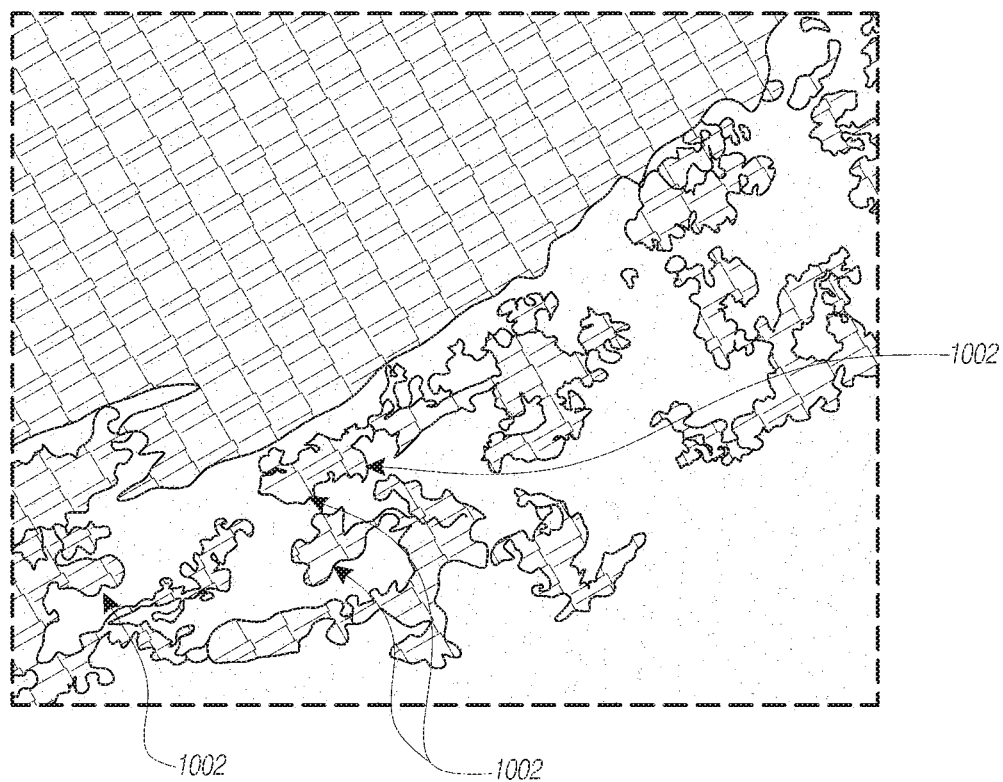
FIG. 11 is an illustration depicting microscopy of the portion identified as S6 of level A9 of the main pulmonary artery of FIG. 9C.

Upon inspection of these samples, it was observed that more SPNDs were identified in the posterior wall in both the left and right pulmonary arteries (FIG. 10A). However the number of SPNDs 1002 was 1.6±0.2 in the S1 subsegment of the A5 level in the left pulmonary artery branch, signifi-cantly different from 1.2±0.2 in the S1 subsegment of level A1 in the right pulmonary artery (p=0.033). In contrast, more SPNDs 1002 were labeled in the anterior wall (S6) of the main pulmonary artery (FIG. 11) and decreased gradually from the levels A9 to A12.

The minor and major radius of sympathetical axons in the main pulmonary artery were 85±2 μm and 175±14 μm, compared to 65±3 μm and 105±12 μm in the left pulmonary artery or 51±2 μm and 86±8 μm in the right pulmonary artery, respectively, resulting in significant differences in surface area of axons between the main pulmonary artery and the LPA and RPA (FIGS. 9A-9C).

Figure 13:
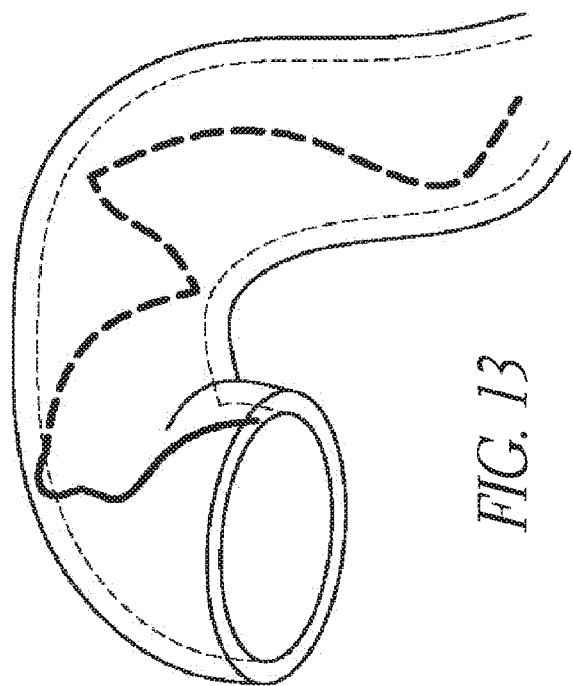
FIG. 13 is an anterior view of the left pulmonary artery of FIG. 12.
Figure 12:
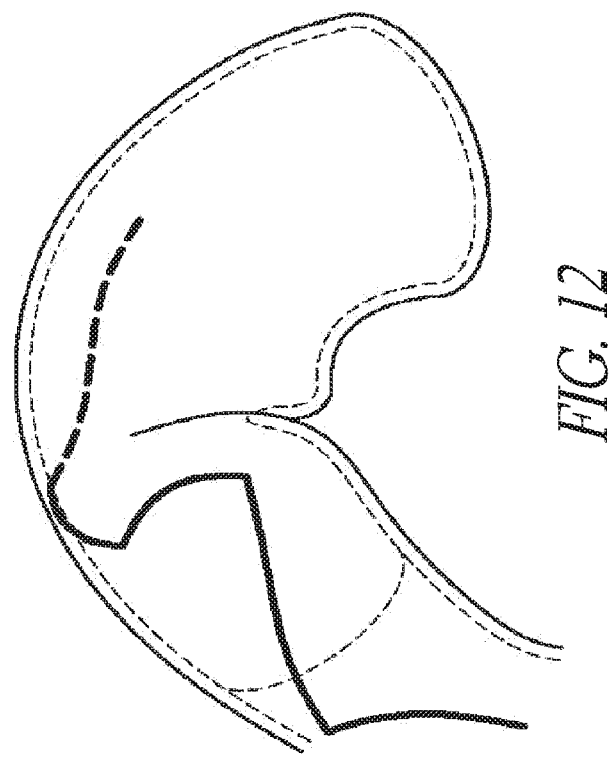
FIG. 12 is a posterior and perspective view of a model of the left pulmonary artery of FIGS. 7A and 7B.

Based on the results of the above-described observations, it has been determined that in canines, sympathetical nerves are distributed in higher concentrations along the anterior wall of the main pulmonary artery, then extend into the left and right pulmonary arteries, then extend upwardly and then toward the posterior walls of the left and right pulmonary arteries, as schematically represented in FIGS. 12 and 13.

Further, inspection of subsegment S6 in level A9 (FIG. 11) of the MPA (magnification 200×) revealed that a bundle or main bundle of sympathetical nerves originate from approximately the middle of the anterior wall of the distal portion of the main pulmonary artery and that this main bundle is bifurcated to the left and right pulmonary arteries.

This discovery provides a basis for more effective denervation of the pulmonary artery. For example, by selectively ablating only portions of the main pulmonary artery and the left and right pulmonary arteries, a higher success rate of denervation can be achieved with less unnecessary tissue damage. Such denervation can provide significant benefits in the treatment of diseases such as pulmonary hypertension, as described below.

With regard to the disease of pulmonary hypertension, it is well known that the lung receives axons from principal sympathetic neurons residing in the middle and inferior cervical and the first five thoracic ganglia (including the stellate ganglion), and the vasculature is the major sympathetic target in the lung. Sympathetic nerve stimulation increases pulmonary vascular resistance and decreases compliance, which is mediated by noradrenaline via a-adrenoreceptors, primarily of the a1-subtype.

Previous studies have confirmed the multiplicity of transmitters released from one nerve ending which might explain why pharmacological blockade of the "classical" transmitter alone does not effectively abolish the effects elicited by nerve stimulation. The present study explained above supports the concept that more successful sympathetical denervation along the pulmonary trunk can be enhanced at the proximal segments of the left and right pulmonary arteries rather than at the distal basal trunks. Further, percutaneous pulmonary denervation (PADN) has potential for decreasing pulmonary pressure and resistance induced by unilateral balloon occlusion in the interlobar artery. However, until now, there was a lack of data showing the distribution of sympathetical nerves in the pulmonary trunk. Thus, the accurate identification of the position of sympathetical nerves is important for performing a successful PADN procedure. In the present study, significantly larger bundles of sympathetical nerves were identified in the mid-anterior wall of the distal portion of the main pulmonary artery, which is bifurcated into the posterior wall of the left and right pulmonary arteries. These results imply that one or more ablation procedures, for example, by PADN, especially around the distal portion of the main pulmonary bifurcation and the proximal portions of the LPA and RPA are more likely to provide enhanced results and more successful denervation, as was suggested in the animal study noted above.

It is noted that sympathetic noradrenergic innervation density is highest at the large extra-pulmonary and hilar blood vessels, both arteries and veins and then decreases toward the periphery. This is in marked contrast to many other organs, in which the highest innervation density is found at the level of the smallest arterioles. Such distribution varies from species to species with regard to the extent to which the sympathetic noradrenergic axons reach into the lung. In guinea pigs, rabbits, sheep, cats, dogs, and humans, small arteries down to 50 μm in diameter are innervated, whereas in rats, mice, hedgehogs, and badgers, noradrenergic innervation stops close to the lung.

An extensive network of noradrenergic and NPY-containing fibers has been noted around pulmonary arteries of several species, but only a few studies used double-labeling techniques to evaluate the extent of colocalization. In the guinea pig, principally all noradrenergic fibers innervating pulmonary arteries and veins contain NPY and, in addition, dynorphin, a neuropeptide of the opioid family. In this aspect, pulmonary vascular innervation differs markedly from that of skin arteries in the same species, wherein three different combinations of noradrenaline, NPY, and dynorphin are used by sympathetic axons. Each of these populations is restricted to a specific segment of the arterial tree in the skin. Still, noradrenergic and NPY-containing fibers do not match 1:1 in the lung either, as there is a minor population of axons innervating guinea pig pulmonary arteries and veins that contains NPY plus vasoactive intestinal peptide (VIP) but not noradrenaline. It remains to be clarified whether this less-frequent fiber population represents the non-noradrenergic neurons projecting to the guinea pig lung or originates from other systems.

The present study explained above, which relied on the serial slicing at various levels through the pulmonary artery trunk demonstrates that larger bundles of nerves are more localized in the anterior wall of the main pulmonary artery and then bifurcate into the left and right pulmonary arteries along the posterior walls of the LPA and RPA. The above study was performed on canine anatomy.

One of the diseases that can be treated with the present methods and devices is idiopathic pulmonary arterial hypertension (IPAH). IPAH is characterized by elevations of mean pulmonary artery pressure (PAP) and pulmonary vascular resistance (PVR). The pathogenesis of IPAH was believed to be due to imbalance between locally produced vasodilators and vasoconstrictors. Recent studies have demonstrated that vascular wall remodeling also contributed to elevated PVR. The role of neural reflex in the mediation and development of IPAH has not been specifically investigated. In 1961, Osorio et al. reported the existence of a pulmo-pulmonary baroreceptor reflex that originates in the large pulmonary branches, with neither the afferent nor efferent fibers belonging to the vagus nerve. In 1980, these findings were again confirmed by Jurastch et al. and Baylen et al. More recently, the present animal study described above demonstrates that pulmonary arterial denervation (PADN) can reduce or completely abolish elevations of PAP induced by balloon occlusion at interlobar segments, but not at the basal trunk.

In a further phase of the present study, a human study was conducted. Prior to enrollment, all 21 patients received a diuretic (hydrochlorothiazide at a dose of 12.5 mg to 25 mg, once daily, and/or spironolactone at a dose of 20 mg to 40 mg, once daily) and beraprost (120 mg, 4 times daily) (Table 1), with either sildenafil (20 mg, 3 times a day) or bosentan (120 mg, twice daily) or digoxin (0.125 mg, once daily). Functional capacity of the patients was determined by a 6-minute walk test (6MWT), followed by an assessment of dyspnea using the Borg scale. The 6MWT was performed at 1 week, 1 month, 2 months, and 3 months following the PADN procedure. The WHO classification at rest and during exercise was recorded by a physician who was blinded to the study design.

Echocardiography was performed at 1 week, 1 month, 2 months, and 3 months following the procedure. Echocardiographic studies were done using a Vivid 7 ultrasound system with a standard imaging transducer (General Electric Co., Easton Turnpike, Conn., US). All of the echocardiograms were performed and interpreted in the Medical University Echocardiographic Laboratory. All of the measurements were performed following the recommendations of the American Society of Echocardiography. Digital echocardiographic data that contained a minimum of 3 consecutive beats (or 5 beats in cases of atrial fibrillation) were acquired and stored. RV systolic pressure is equal to systolic PAP in the absence of pulmonary stenosis. Systolic PAP is equal to the sum of right atrial (RA) pressure and the RV to RA pressure gradient during systole. RA pressure was estimated based on the echocardiographic features of the inferior vena cava and assigned a standard value. The RV to RA pressure gradient was calculated as $4 v_t^2$ using the modified Bernoulli equation, where $v_t$ is the velocity of the tricuspid regurgitation jet in m/s. The mean PAP was estimated according to the velocity of the pulmonary regurgitation jet in m/s. The tricuspid excursion index (TEI) is defined as (A−B)/B, where A is the time interval between the end and the onset of tricuspid annular diastolic velocity, and B is the duration of tricuspid annular systolic velocity (or the RV ejection time). PA compliance for patients was calculated as stroke volume divided by pulse pressure (systolic PAP minus diastolic PAP).

Hemodynamic measurements and blood oxygen pressure/saturation determinations from the RA, RV, and PA were done prior to and immediately after the PADN procedure. These measurements were repeated at 24 hours and 3 months.

A 7F flow-directed Swan-Ganz catheter (131HF7, Baxter Healthcare Corp., Irvine, Calif.) was inserted into an internal jugular or subclavian vein. Measurements of resting RA pressure, RV pressure, systolic/diastolic/mean PAP, pulmonary artery occlusive pressure (PAOP), cardiac output (CO) (using thermodilution method), and mixed venous oxygen saturation were recorded. The PVR [=(mean PAP−PAOP)/CO] and trans-pulmonary gradient (TPG=mean PAP−PAOP) were then calculated. All of the measurements were recorded at the end of expiration. Five criteria were used to evaluate if a PAOP measurement was valid: (1) the PAOP was less than the diastolic PAP; (2) the tracing was comparable to the atrial pressure waveform; (3) the fluoroscopic image exhibited a stationary catheter following inflation; (4) free flow was present within the catheter (flush test); and (5) highly oxygenated blood (capillary) was obtained from the distal portion in the occlusion position. If the PAOP measurement was unreliable, the left ventricular end-diastolic pressure was then measured and used rather than the PAOP. The blood samples from the SVC and pulmonary artery were obtained for the measurements of oxygen pressure and saturation. Particularly significant reductions in systolic and mean PAP were achieved using temperatures above 50° C., drawing an electrical load of 8-10 W for a duration of 60-120 s, for example as shown in FIG. 14B.

The PADN procedure was performed with a dedicated 7.5 F multiple-function (temperature-sensor and ablation) catheter which comprised two parts, a catheter shaft 3 and handle 2 (FIG. 15A) which is an embodiment of the catheter illustrated in FIGS. 1-4. The catheter of FIG. 15A had a tapered (to 5 F) annular ring 4 with 10 pre-mounted electrodes 5 (E1-E10) each separated by 2 mm, however, other spacings can also be used. For purposes of the description set forth below, the electrodes 5 have been numbered, as shown in FIG. 15B, with the distal-most electrode 5 identified as electrode E1 and the proximal-most electrode 5 identified as electrode E10.

As described above with reference to FIGS. 1-4, the annular ring 4 or ("circular tip") can be constructed so as to be biased into a circular shape, such as the circular shape illustrated in FIG. 15B and FIG. 1 to have any desired outer diameter. For example, in various embodiments, the annular ring 4 can be configured to be biased into a circular shape having an outer diameter of 20 mm, 25 mm, 30 mm, 35 mm, 40 mm, 45 mm, or other diameters. Additionally, a kit containing the catheter of FIG. 1 can include a plurality of different annular rings 4 configured to be biased to a plurality of different outer diameters, such as those noted above, or other diameters.

A controller or "connect box" can be connected to the handle 2 of the catheter for providing ablation energy. For example, an ablation controller 100 can be configured to provide ablation energy to each of the electrodes E1-E10. Thus, in some embodiments, the controller 100 includes a selector knob 102 configured to allow a user to select activation of all the electrodes E1-E10, or selective actuation of individual ones of the electrodes E1-E10, one at a time.

Thus, in some embodiments, as illustrated in FIG. 15D, the selector knob 102 includes a position indicator 104 which, by rotating the knob 102 can be aligned with indicia corresponding to the electrodes E1-E10. In the illustrated embodiment, the indicia on the controller 100 includes the numbers 1-10 as well as a position identified as "OFF" and a position identified as "NULL." In some embodiments, the connect cable 106 can include a plurality of wires, for example, ten wires which correspond to the lead wire 6 described above with reference to FIGS. 1-4, each one of which is individually connected to respective electrodes E1-E10.

The controller 100 can include a physical switch for creating an electrical connection between a source of RF energy and a desired one of the electrodes E1-E10. An electrode (not shown) can be directly connected to the knob 102 with additional contacts (not shown) disposed around the electrode at approximately the positions identified as 1 through 10 on the controller 100. Thus, rotation of the knob 102 will connect an internal electrode (not shown) with the contacts aligned with each one of the positions 1-10.

The controller 100 can be configured to provide the desired amount of ablation energy when a circuit is created by the alignment of the position indicator 104 with the corresponding position (1 through 10) on the controller 100 thereby delivering electrical energy to the selected one of the electrodes E1-E10 causing electrical energy to pass through the selected electrode 5 into any conductive material in contact with that selected electrode.

For example, during a PADN procedure, the electrodes E1-E10 can be in contact with an inner wall of the pulmonary artery trunk thereby allowing electrical energy from one of the electrodes E1-E10 to flow through the tissue of the inner wall of the pulmonary artery, described in greater detail below.

In some embodiments, with continued reference to FIG. 15D, the controller 100 can include a plurality of ports. For example, the controller 100 can include a catheter port 120, which can be configured for creating a fluidic connection to the annular ring for purposes of providing a flow of saline to the annular ring 4. The controller 100 can also include an RF port 122 configured to connect to any known radiofrequency generator used with regard to ablation procedures.

Additionally, the controller 100 can include an "ECG" port 124 configured for connection with standard ECG monitoring equipment. Thus, in some embodiments, the connect cable 106 can also include wires or conduits for transmitting data through the RF port 124.

Thus, in some configurations, the RF port 122 can be connected to a source of RF energy (not shown). One or more wires (not shown) can connect the port 122 to a contact on the end of an electrode connected to the selector knob 102. Additionally, the ten wires (not shown) can be configured to deliver RF electrical energy to the electrodes E1-E10 each of which can each be connected to contacts (not shown) associated with the selector positions 1-10 disposed around the periphery of the selector knob 102.

Thus, the electrode connected to the rotating selector knob 102 cab be moved into contact with the electrical contacts associated with each of the positions 1-10 thereby creating a circuit connecting the electrical energy entering the controller 100 through the port 122 with the associated lead wire 6 for conducting electrical energy to the desired electrode E1-E10.

Thus, specifically, when the selector knob 102 is turned such that the position indicator 104 is aligned with position 1 on the controller 100, electrical energy from the RF port 122 is conducted through an associated lead wire 6 to the electrode E1. Aligning the indicator 104 with the other positions on the controller 100 would conduct electrical energy to the other electrodes associated with those other positions.

In some embodiments, a method for treating pulmonary hypertension can include a step of identifying the position of the pulmonary trunk of the patient using angiography. For example, baseline pulmonary artery angiography can be performed to identify the position of the pulmonary artery bifurcation from the main pulmonary artery into the left and right pulmonary arteries.

Additionally, the baseline pulmonary artery angiography can be used to determine the diameter of the portions of the pulmonary artery trunk upon which ablation is desired. As such, the appropriate diameter of the annular ring 4 can be determined based on the determined diameters of the pulmonary artery trunk noted above. For example, in some embodiments, an annular ring 4 having a biased diameter slightly larger than the diameters of the targeted anatomy can be used so as to enhance the contact between the electrodes 5 and the inner surface of the targeted anatomy. As such, for example, when the annular ring 4 is moved out of a sheath and allowed to expand into its biased circumferential configuration which has an outer diameter slightly larger than the inner diameter of the targeted portions of the pulmonary artery trunk, the bias of the annular ring 4 will assist in pressing the electrodes 5 into contact with the targeted tissue.

Figure 16A:
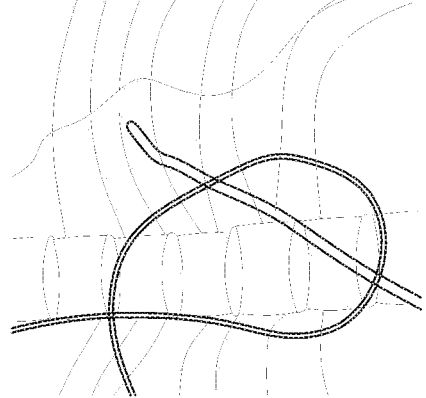
FIG. 16A is an illustration depicting a fluoroscope image of a sheath device inserted into the main pulmonary artery for guiding the catheter device of FIG. 15A into the main pulmonary artery.

In some embodiments, with reference to FIGS. 16A-16H, a method can include a step of positioning a catheter in a pulmonary artery trunk. For example, an 8F long sheath can be inserted through the femoral vein and advanced to the main pulmonary artery, as shown in FIG. 16A. A PADN catheter, such as the catheter illustrated in FIG. 1 and FIGS.

15A-15E can be advanced along the sheath shown in FIG. 16A to the location of the pulmonary artery trunk.

With the distal end of the catheter maintained in place, the sheath can be withdrawn. It may be necessary to push on the catheter to maintain its position with the portion of the catheter forming the annular ring 4 held within the pulmonary artery trunk.

Figure 16B:
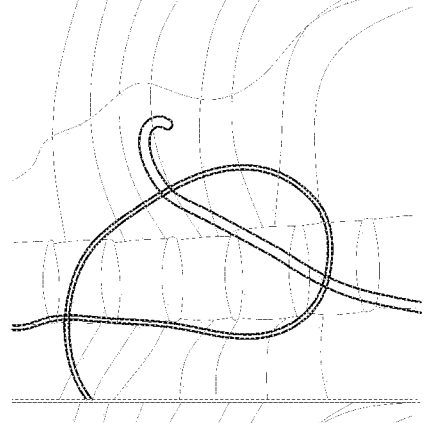
FIGS. 16B-16D are illustrations depicting additional fluoroscope images of the catheter device of FIG. 15A having been inserted and expanded within the left pulmonary artery of a human patient.
Figure 16C:
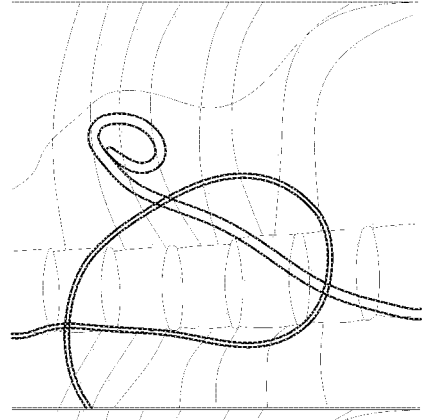

As the annular ring 4 is released from the sheath, as illustrated in FIG. 16B, the annular ring 4 can adopt the shape and diameter to which it is biased.

Figure 16D:
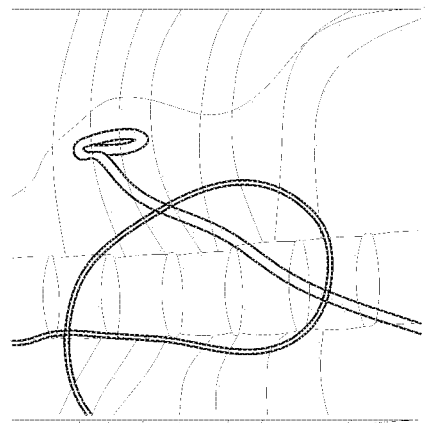

By slightly rotating and pushing the handle 2 in a clockwise direction, the annular ring 4 can be positioned at the proximal portion of the left pulmonary artery, such as at the ostium. In some embodiments, this initial position can be within a range of approximately five mm from the orifice of the left pulmonary artery or within a range of two millimeters, as illustrated in FIG. 16D.

By observing the orientation of the annular ring 4, the desired one or plurality of the electrodes E1-E10 can be selectively energized so as to perform ablation at the desired location on the interior surface of the left pulmonary artery. For example, in some embodiments, it may be more effective to selectively ablate the posterior wall of the left pulmonary artery, so as to achieve at least some sympathetic denervation of the left pulmonary artery and the proximal portion thereof, such as within two or five millimeters of the ostium of the left pulmonary artery.

Figure 16E:
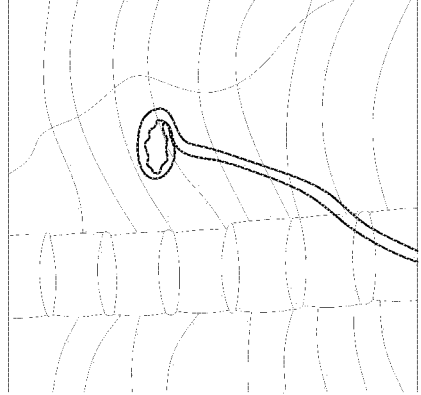
FIG. 16E illustrates the catheter of FIG. 15A being positioned within the main pulmonary artery of the patient in a position used for ablation.

The annular ring 4 can then be rotated, such as in the counterclockwise direction, by rotating and withdrawing the handle 2 in order to reposition the annular ring 4 into the distal portion of the main pulmonary artery such as at the bifurcation area. For example, in some embodiments, as illustrated in FIG. 16E, the annular ring 4 can be positioned within about 5 mm of the bifurcation in the pulmonary artery trunk. Optionally, the annular ring 4 can be positioned within about 5 mm of the bifurcation in the pulmonary artery trunk. Ablation can then be performed using the desired one or plurality of the electrodes E1-E10.

For example, positioned as such, the selected one or plurality of electrodes E1-E10 can be energized to achieve the desired sympathetic denervation of the distal portion of the main pulmonary artery. In some embodiments, it may be desirable to perform ablation preferentially on the anterior wall of the distal portion of the main pulmonary artery.

Additionally, further rotating and pushing the handle 2 can be performed until the annular ring 4 is positioned in the proximal portion of the right pulmonary artery, such as at the ostium. In some embodiments, this position can be within 5 mm of the ostium of the right pulmonary artery. Further, in some embodiments, this position can be within 2 mm of the ostium of the right pulmonary artery.

With the annular ring 4 positioned as such, the desired one or plurality of electrodes E1-E10 can be energized so as to achieve at least some sympathetic denervation in the proximal portion of the right pulmonary artery. For example, in some embodiments, it may be beneficial to focus on the posterior wall of the right pulmonary artery.

In some embodiments, a method for treating pulmonary hypertension can also include a step of confirming the appropriate contact between the electrodes E1-E10 and the endovascular surface corresponding to the three positions noted above. For example, in some embodiments, such confirmation can be performed by determining if there is strong manual resistance when attempting to rotate the handle 2. Additionally, it can be determined if the annular ring 4 cannot be advanced distally, resulting in the deformation of the catheter as illustrated in FIG. 16G or if there is ease in withdrawing proximally, resulting in the deformation of the catheter illustrated in 16H. Additionally, confirmation can be performed using angiographic confirmation.

Figure 16F:
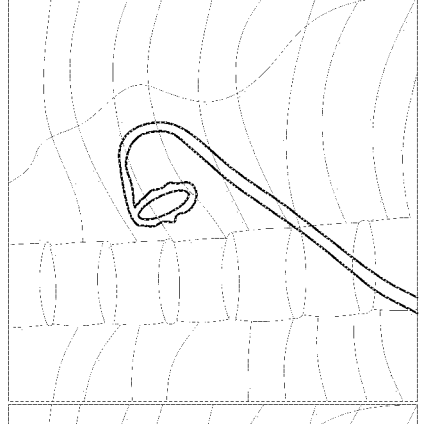
FIGS. 16F and 16G illustrate the catheter of FIG. 15A being positioned in the proximal right pulmonary artery and being pushed (FIG. 16F) and pulled (FIG. 16G) to determine if the catheter is properly seated for purposes of ablation.
Figure 16G:
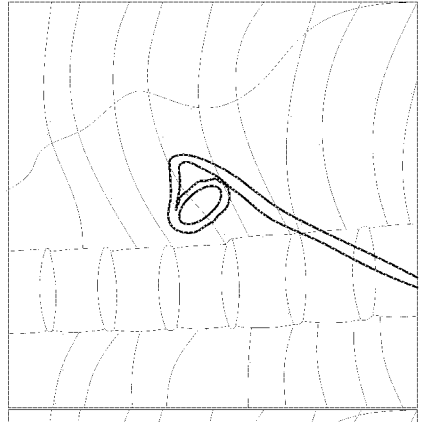
Figure 16H:
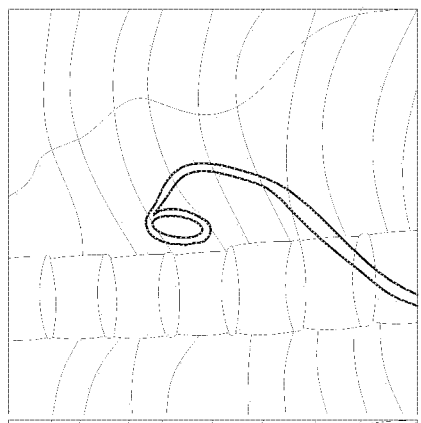
FIG. 16H is an illustration depicting a fluoroscope image of the catheter of FIG. 15A in a position for performing ablation in a proximal portion of the right pulmonary artery.

When the appropriate contact has been confirmed with the annular ring 4 is positioned as desired such as in the positions illustrated in FIGS. 16D, 16E and 16F, at least one of the electrodes E1-E10 can be energized so as to perform ablation. For example, in some embodiments, a method for treating pulmonary hypertension can include the sequential energization of each of the electrodes E1-E10.

Additionally, in some embodiments, a method for treating pulmonary hypertension or for performing pulmonary denervation can include the step of repositioning the annular ring 4 so as to shift the location of the electrodes E1-E10 and then repeating energization of all of the electrodes E1-E10. As such, a more complete denervation of the entire inner surface of the associated vessel can be achieved.

In some embodiments, any desired energy levels or temperatures can be used for performing ablation using the electrodes E1-E10 noted above. For example, in some embodiments, ablation can be performed at temperatures above 50° C., drawing an electrical load of 8-10 W for a duration of 60-120 s. Additionally, in some embodiments, a method of treatment of pulmonary hypertension or a method of sympathetic denervation of the pulmonary artery can be performed with a patient anesthetized but conscious. Thus, any ablation procedure can be stopped if the patient complained of intolerable chest pain.

In some embodiments, EKG and hemodynamic pressure can be monitored and continuously recorded throughout the method. In a study performed in accordance with the description noted above, success was defined as a reduction in the mean PAP≥10 mmHg (as measured by the Swan-Ganz catheter). During the study, there were no complications. Additionally, the patients were monitored in the CCU for at least 24 hours after the PADN procedure was performed.

For example, in some embodiments of methods disclosed herein, a dedicated 7.5 F triple-function catheter (A) can be used, which can include a tapered (to 5 F) annular ring 4 with 10 electrodes (each has 0.75 mm electrode-width and is separated by 2-mm, B), pre-mounted. Electrodes are connected with a connect-cable 106 and a connect-box/controller 100. There are 10 positions of the knob 102 (FIG. 15D) on the surface of controller 100, and each is associated with one of the electrodes E1-E10 on the annular ring 4 of the ablation catheter. Sequential ablation can be performed by turning the knob 102 as desired after the whole system is set up.

In some embodiments of methods for performing pulmonary artery denervation or methods for treating primary PAH ablation of the distal portion of the main pulmonary artery can be performed preferentially on the anterior side thereof. For example, in some embodiments, as shown in FIG. 17A, ablation can be performed at the positions identified as M1, M2, M3, M4, and M5.

Figure 17A:
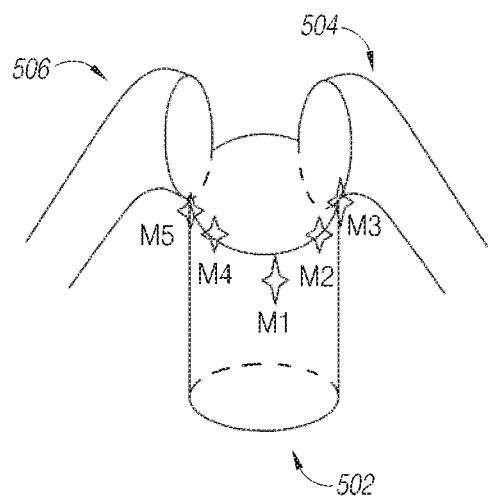
FIG. 17A is a schematic diagram of the trunk of a pulmonary artery and identifying locations for ablation in a distal portion of a main pulmonary artery.

With a continued reference to FIG. 17A, the position identified as M1 is at the "6 o'clock" position in the distal portion of the main pulmonary artery. The positions identified as M3 and M5 are the sites where the anterior wall of the main pulmonary artery connects to the left and right pulmonary arteries, respectively. The positions identified as M2 and M4 correspond to the "5 o'clock" and the "7 o'clock" positions on the anterior side of the distal portion of the main pulmonary artery.

Figure 17B:
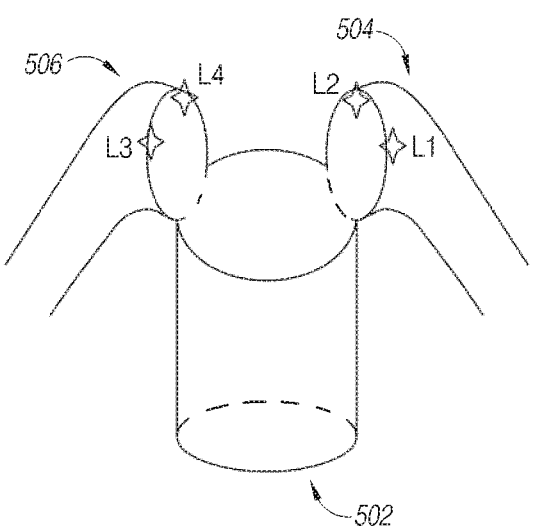
FIG. 17B is a schematic diagram of a pulmonary artery trunk and identifying locations for ablation in proximal portions of the left and right pulmonary arteries.

In some embodiments, with reference to FIG. 17B, sympathetic denervation in the left and right pulmonary arteries can be performed, preferentially, at approximately the middle of the anterior wall of the proximal portion of the left pulmonary artery (L1) and at approximately the upper conjunctive site of the distal portion of the main pulmonary artery in the left pulmonary artery (L2).

Similarly, during a method of performing pulmonary denervation of the right pulmonary artery, ablation can be preferentially performed at a point approximately at the middle anterior wall of the proximal portion of the right pulmonary artery (L3) and at approximately the upper conjunctive site of the distal portion of the main pulmonary artery and the right pulmonary artery (L4).

In some embodiments, sympathetic denervation can be performed, for example, for treatment of pulmonary hypertension associated with a pulmonary duct artery (PDA) 1802. For example, a pulmonary duct artery usually connects the descending aorta with the left pulmonary artery, as shown in FIG. 4A. With this anatomy, the left pulmonary artery can be significantly larger than the right pulmonary artery.

Figure 18A:
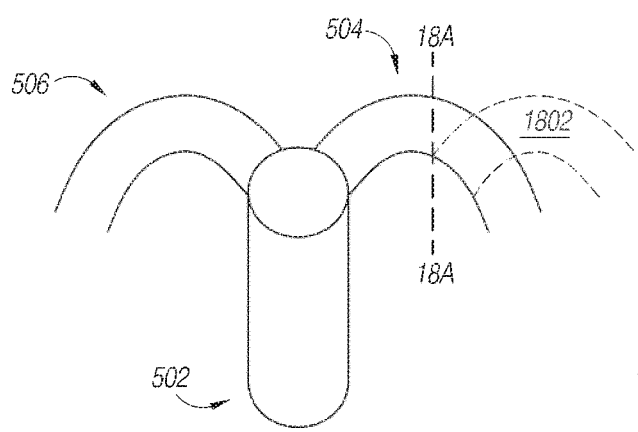
FIG. 18A is a schematic diagram of a pulmonary artery trunk identifying a position for ablation in a portion of the left pulmonary artery proximal to a pulmonary artery duct.

Thus, in some embodiments, ablation can be performed at a position proximal to connection between the left pulmonary artery and the pulmonary duct artery, identified by line 18A-18A in FIG. 18A and referred to as "Level A". Thus, using the technique described above with reference to FIGS. 16A-16H, the annular ring 4 can be positioned at a position corresponding to Level A of FIG. 18B. Ablation can then be performed around part or all of the interior wall of the left pulmonary artery at that location.

Figure 18B:
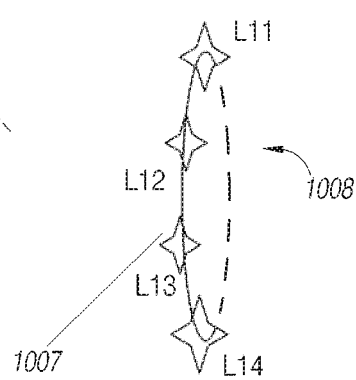
FIG. 18B is a schematic diagram of points of ablation in the anterior wall of the ablation position identified in FIG. 18A.

In some embodiments, ablation can be preferentially performed on the anterior wall of the left pulmonary artery proximal to the proximal end of the pulmonary duct artery. For example, ablation can be performed at four or more sites, such as those identified as sites L1, L2, L3, L4. As illustrated in FIG. 18B, which shows an anterior wall 1007 and a posterior wall 1008, position L11 corresponds to "12 o'clock", position L12 corresponds to "2 o'clock", position L13 corresponds to "3 o'clock", and position L14 corresponds to "6 o'clock." Other positions can also be used.

Additionally, in some embodiments, ablation can also be performed at positions M1-M5 illustrated in FIG. 17A and positions L1-L4 of FIG. 17B.

Figure 19A:
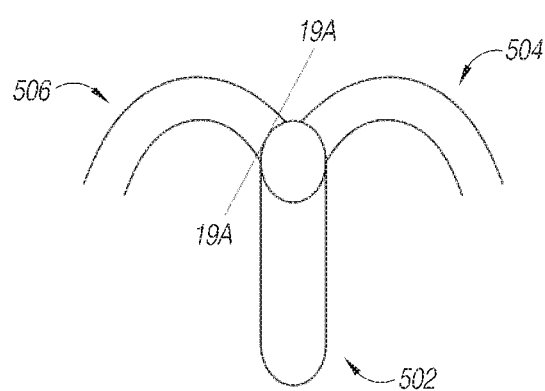
FIG. 19A is a schematic diagram of a pulmonary artery trunk identifying a position for ablation in a proximal portion of the right pulmonary artery for treatment of unilateral chronic thrombotic embolism.
Figure 19B:
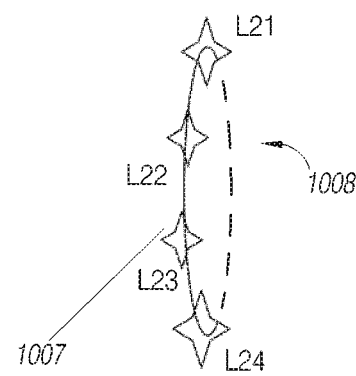
FIG. 19B is an enlarged schematic diagram of the portion identified in FIG. 19A and indicating positions for ablation in the anterior wall of the proximal portion of the right pulmonary artery.

In some embodiments, a method for sympathetic denervation can be used for treating pulmonary hypertension resulting from unilateral chronic thrombotic embolism. For example, a patient suffering from unilateral CTEH can have an occluded right pulmonary artery. For example, in some patients, the RPA can be significantly enlarged as illustrated on the left side of FIG. 19A. Similarly to the method described above with reference to FIG. 18B, ablation can be performed at the position identified by line 19A-19A in FIG. 19A and referred to as "Level B". Ablation can be performed at one or a plurality of locations along the inner surface of the right pulmonary artery at the position of Level B, or other positions. Additionally, ablation can be preferentially performed on a plurality of points along the anterior wall of the right pulmonary artery at the position of Level B.

For example, the positions identified in FIG. 20B can be considered such as position L1 corresponding to "12 o'clock", position L2 corresponding to "2 o'clock", position L3 corresponding to "3 o'clock", and position L4 corresponding to "6 o'clock." Additionally, in some embodiments, ablation can also be performed at positions M1-M5 illustrated in FIG. 17A and positions L1 and L2 illustrated in FIG. 17B.

As used herein, the term "animal" is intended to include human beings and other animals such canines, other mammals, etc. As used herein, the terms "live", "living", "live animal" are intended to exclude methods of euthanasia, surgery performed on dead animals including dissection and autopsies, or other techniques for disposing of dead bodies.

While at least a plurality of different embodiments are disclosed herein, it should be appreciated that a vast number of variations exist. It should also be appreciated that the embodiments described herein are not intended to limit the scope, applicability, or configuration of the claimed subject matter in any way. Rather, the foregoing detailed description will provide those skilled in the art with a convenient road map for implementing the described embodiments. It should be understood that various changes can be made in the function and arrangement of elements or steps without departing from the scope defined by the claims, which includes known equivalents and foreseeable equivalents at the time of filing this patent application.

What is claimed is:

1. A method of performing pulmonary artery denervation comprising:
    positioning an ablation device in a pulmonary artery trunk of a patient, the pulmonary artery trunk including a distal portion of a main pulmonary artery, a proximal portion of a left pulmonary artery, and a proximal portion of a right pulmonary artery; and
    ablating target tissue in the pulmonary artery trunk under conditions effective to affect a reduction in mean pulmonary artery pressure of the patient,
    wherein the target tissue comprises at least one of the distal portion of the main pulmonary artery, the proximal portion of the left pulmonary artery, or the proximal portion of the right pulmonary artery with the ablation device,
    wherein the conditions effective to affect the reduction in mean pulmonary artery pressure also affect a reduction in systolic pulmonary artery pressure.

2. The method of claim 1, wherein the reduction in mean pulmonary artery pressure is about 10%.

3. The method of claim 1, wherein the reduction in mean pulmonary artery pressure is about 30%.

4. The method of claim 1, wherein the reduction in systolic pulmonary artery pressure is about 10%.

5. The method of claim 1, wherein the reduction in systolic pulmonary artery pressure is about 30%.

6. The method of claim 1, wherein ablating the target tissue comprises ablating the target tissue at a temperature of about 50° degrees C. to about 60° degrees C.

7. The method of claim 1, wherein ablating the target tissue comprises ablating the target tissue with an energy of between about 8 W to about 10 W.

8. The method of claim 1, wherein ablating the target tissue comprises ablating the target tissue for between about 60 and about 120 seconds.

9. The method of claim 1, wherein ablating the target tissue comprises applying at least one of radiofrequency (RF) energy, microwave energy, ultrasound energy, focused ultrasound energy, ionizing energy, electroporation, a drug, a chemical agent, or cryoablation to the target tissue.

10. The method of claim 1, wherein ablating the target tissue causes disruption of sympathetic nerves at the pulmonary artery trunk.

11. The method of claim 1, wherein ablating the target tissue comprises generating a continuous ablation pattern.

12. The method of claim 1, wherein ablating the target tissue comprises generating a non-continuous ablation pattern.

13. The method of claim 1, wherein ablating the target tissue comprises ablating the target tissue with a distal annular ring of the ablation device, the distal annular ring comprising one or more ablation electrodes.

14. The method of claim 1, wherein positioning the ablation device in the pulmonary artery trunk of the patient comprises passing the ablation device into a femoral vein of the patient, upwardly into an inferior vena cava of the patient, then upwards into a right atrium of the patient, then down into a right ventricle of the patient, and then up through a pulmonary semilunar valve of the patient to the main pulmonary artery trunk.

15. The method of claim 1, further comprising visualizing at least one of the main pulmonary artery trunk or the ablation device positioned in the main pulmonary artery trunk to confirm to positioning of the ablation device.

16. The method of claim 1, further comprising visualizing the main pulmonary artery prior to positioning the ablation device in the pulmonary artery trunk.

17. The method of claim 1, wherein the main pulmonary artery is visualized with one or more of magnetic resonance imaging (MRI) or computed tomograpghy (CT) scanning.

18. The method of claim 1, further comprising withdrawing the ablation device from the main pulmonary artery after the target tissue has been ablated.

19. The method of claim 18, further comprising visualizing the main pulmonary artery after the ablation device has been withdrawn.

20. The method of claim 1, wherein the ablated target tissue comprises the distal portion of the main pulmonary artery and the proximal portion of the left pulmonary artery.

21. The method of claim 1, wherein the ablated target tissue comprises the distal portion of the main pulmonary artery and the proximal portion of the right pulmonary artery.

22. The method of claim 1, wherein the ablated target tissue comprises the proximal portion of the left pulmonary artery and the proximal portion of the right pulmonary artery.

23. The method of claim 1, wherein the ablated target tissue comprises the distal portion of the main pulmonary artery, the proximal portion of the left pulmonary artery, and the proximal portion of the right pulmonary artery.

24. The method of claim 1, wherein ablating the target tissue comprises ablating an anterior wall of the distal portion of the main pulmonary artery.

25. The method of claim 1, wherein ablating the target tissue comprises ablating a posterior wall of the right pulmonary artery.

26. The method of claim 1, wherein positioning the ablation device comprises positioning a distal annular ring adjacent the target tissue.

27. The method of claim 26, wherein positioning the distal annular ring comprises one or more of rotating or pushing a handle of the ablation device.

* * * * *